US009526524B2

(12) United States Patent
Khatchadourian et al.

(10) Patent No.: US 9,526,524 B2
(45) Date of Patent: Dec. 27, 2016

(54) ADJUSTABLE ROD ASSEMBLY

(71) Applicant: DePuy Synthes Products, Inc., Raynham, MA (US)

(72) Inventors: Roberto Khatchadourian, West Chester, PA (US); Edward J. McShane, West Chester, PA (US); David Rathbun, Gap, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/607,413

(22) Filed: Jan. 28, 2015

(65) Prior Publication Data

US 2015/0134002 A1 May 14, 2015

Related U.S. Application Data

(63) Continuation of application No. 12/610,888, filed on Nov. 2, 2009, now Pat. No. 8,974,500.

(60) Provisional application No. 61/110,711, filed on Nov. 3, 2008.

(51) Int. Cl.
*A61B 17/70* (2006.01)
(52) U.S. Cl.
CPC ......... *A61B 17/7014* (2013.01); *A61B 17/707* (2013.01); *A61B 17/7047* (2013.01); *A61B 17/7055* (2013.01); *A61B 17/7056* (2013.01); *A61B 17/7083* (2013.01)
(58) Field of Classification Search
CPC ............ A61B 17/7014; A61B 17/7047; A61B 17/7055; A61B 17/7056; A61B 17/707; A61B 17/7083

USPC ................. 606/60, 246, 248, 258, 256, 259, 260,606/261, 263, 276, 277, 278, 279, 74
See application file for complete search history.

(56) References Cited

U.S. PATENT DOCUMENTS

| 4,433,677 | A | 2/1984 | Ulrich et al. |
| 5,030,235 | A | 7/1991 | Campbell, Jr. |
| 5,092,889 | A | 3/1992 | Campbell, Jr. |
| 5,102,412 | A | 4/1992 | Rogozinski |
| 5,133,716 | A | 7/1992 | Plaza |
| 5,192,305 | A | 3/1993 | Sastre |

(Continued)

FOREIGN PATENT DOCUMENTS

| CN | 102245117 | 11/2011 |
| EP | 2352449 | 8/2011 |

(Continued)

OTHER PUBLICATIONS

U.S. Appl. No. 61/110,711, filed Nov. 3, 2008, Khatchadourian et al.

(Continued)

*Primary Examiner* — Pedro Philogene
*Assistant Examiner* — David C Comstock
(74) *Attorney, Agent, or Firm* — Baker & Hostetler LLP

(57) ABSTRACT

An adjustable rod for spinal corrective surgery is provided that includes a first elongate member and a second elongate member, each having rod portions couplable to one or more bone connecting elements and expansion portions slideably movable with respect to one another. A plurality of holes in each expansion portion are alignable with one another to choose the length of the adjustable rod and a locking element is inserted through a pair of aligned holes to couple the first and second elongate members and secure or fix the length of the expandable rod.

20 Claims, 16 Drawing Sheets

(56) References Cited

U.S. PATENT DOCUMENTS

| | | |
|---|---|---|
| 5,261,908 A | 11/1993 | Campbell, Jr. |
| 5,290,288 A | 3/1994 | Vignaud et al. |
| 5,330,472 A | 7/1994 | Metz-Stavenhagen |
| 5,498,262 A * | 3/1996 | Bryan ............... A61B 17/1757 606/250 |
| 5,632,744 A | 5/1997 | Campbell, Jr. |
| 5,800,434 A | 9/1998 | Campbell, Jr. |
| 5,810,815 A | 9/1998 | Morales |
| 5,976,125 A | 11/1999 | Graham |
| 6,126,660 A | 10/2000 | Dietz |
| 6,158,437 A | 12/2000 | Vagley |
| 6,224,597 B1 | 5/2001 | Coker |
| 6,238,396 B1 | 5/2001 | Lombardo |
| 6,264,658 B1 | 7/2001 | Lee et al. |
| 6,402,751 B1 | 6/2002 | Hoeck et al. |
| 6,592,585 B2 | 7/2003 | Lee et al. |
| 6,887,241 B1 | 5/2005 | McBride et al. |
| 6,991,632 B2 | 1/2006 | Ritland |
| 7,011,658 B2 | 3/2006 | Young |
| 7,104,993 B2 * | 9/2006 | Baynham ........... A61B 17/7052 606/252 |
| 7,118,571 B2 | 10/2006 | Kumar et al. |
| 8,016,837 B2 | 9/2011 | Giger et al. |
| 8,956,392 B2 | 2/2015 | Khatchadourian et al. |
| 8,974,500 B2 | 3/2015 | Khatchadourian et al. |
| 2003/0153917 A1 | 8/2003 | Richelsoph et al. |
| 2004/0078040 A1 | 4/2004 | Feijtel |
| 2004/0133203 A1 | 7/2004 | Young et al. |
| 2004/0153067 A1 * | 8/2004 | Smith ................ A61B 17/8076 606/60 |
| 2005/0080416 A1 | 4/2005 | Ryan et al. |
| 2006/0089717 A1 | 4/2006 | Krishna et al. |
| 2006/0195087 A1 | 8/2006 | Sacher et al. |
| 2006/0195088 A1 | 8/2006 | Sacher et al. |
| 2007/0239161 A1 | 10/2007 | Giger et al. |
| 2007/0270803 A1 | 11/2007 | Giger et al. |
| 2007/0270808 A1 | 11/2007 | Drewry et al. |
| 2008/0027436 A1 | 1/2008 | Cournoyer et al. |
| 2008/0033434 A1 | 2/2008 | Boomer et al. |
| 2008/0045951 A1 | 2/2008 | Fanger et al. |

FOREIGN PATENT DOCUMENTS

| | | |
|---|---|---|
| JP | 2000-501624 | 2/2000 |
| JP | 2004-504884 | 2/2004 |
| JP | 2012-507374 | 3/2012 |
| KR | 10-2007-0097293 | 10/2007 |
| KR | 20110093826 | 8/2011 |
| WO | WO 93/22989 | 12/1993 |
| WO | WO 98/52482 | 11/1998 |
| WO | WO 2006/116437 | 11/2006 |
| WO | WO 2009/015100 | 1/2009 |
| WO | WO 2010/062718 | 6/2010 |

OTHER PUBLICATIONS

VEPTR, "Vertical Expandable Prosthetic Titanium Rib Technique Guide", Synthes Spine; dated 2005.

VEPTR II, "Vertical Expandable Prosthetic Titanium Rib II Technique Guide", Synthes Spine; dated Apr. 2008.

Pediatric Isola® Spinal System Brochure, Acromed, Feb. 1998, 8 pages.

* cited by examiner

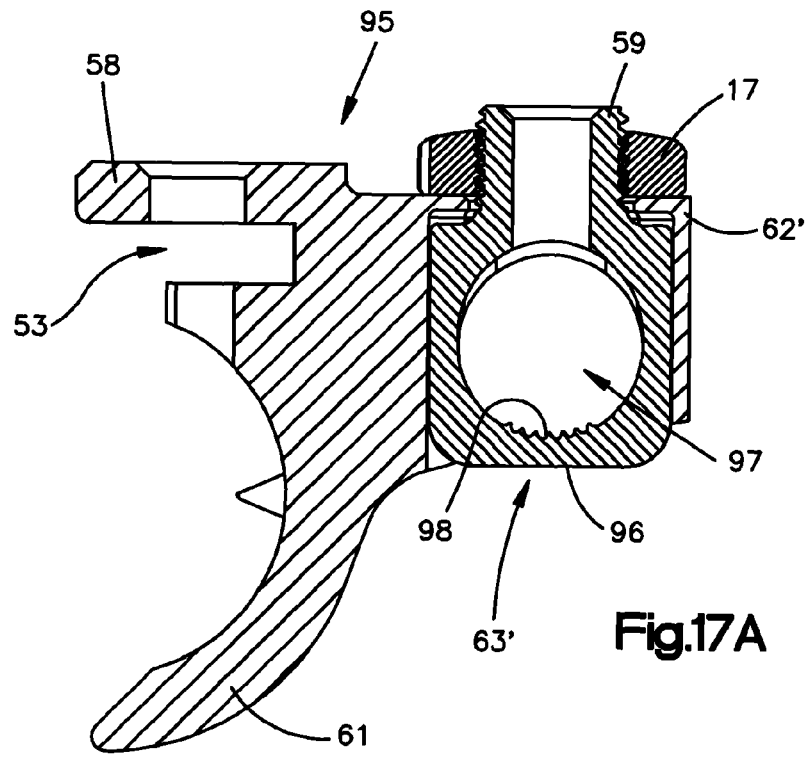
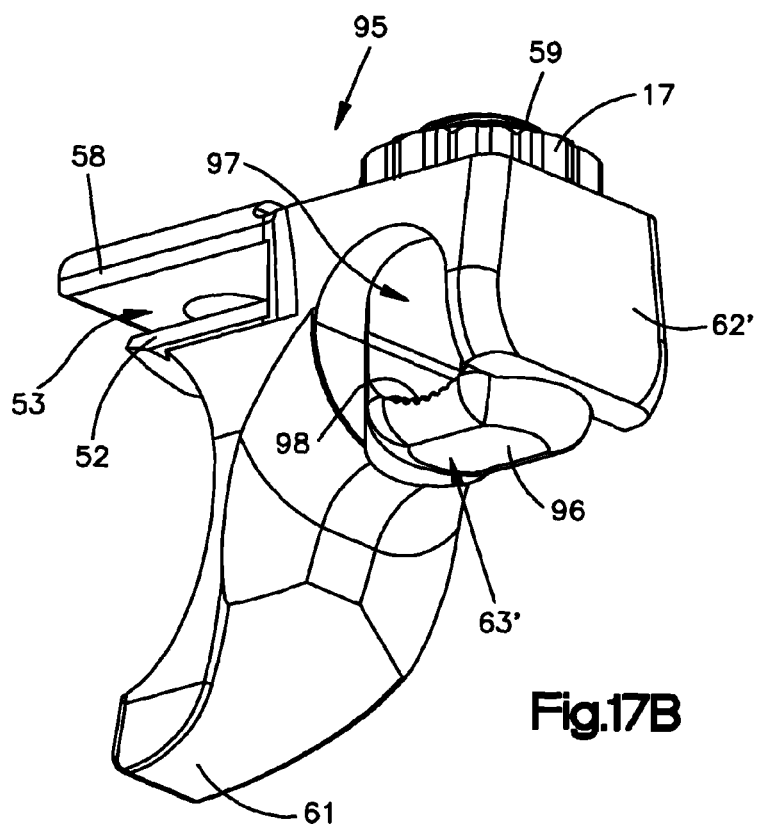

ADJUSTABLE ROD ASSEMBLY

CROSS REFERENCE TO RELATED APPLICATIONS

This application is a continuation of U.S. patent application Ser. No. 12/610,888 filed Nov. 2, 2009, entitled "Adjustable Rod Assembly" which claims the benefit of U.S. Provisional Patent Application Ser. No. 61/110,711, filed on Nov. 3, 2008, entitled "Adjustable Rod For Spinal Correction", which are incorporated in their entireties by reference thereto.

BACKGROUND OF THE INVENTION

It is desirable to provide an elongate spinal fixation rod for use in spinal deformity correction that is adjustable in size to allow adjustments to be made intraoperatively, as well as postoperatively to accommodate the spine as it grows or as the deformity is corrected.

It is further desirable to facilitate percutaneous insertion of an adjustable rod to reduce the invasiveness of the surgery as well as to reduce the occurrence of postoperative infection. Accordingly, an adjustable rod assembly that is configured for percutaneous implantation is desirable.

BRIEF SUMMARY OF THE INVENTION

The present invention relates generally to orthopedics. More specifically, a preferred embodiment of the present invention relates to an adjustable elongated assembly for deformity correction. The adjustable elongated assembly, also interchangeably referred to as an adjustable rod assembly, is preferably used for correcting or straightening a human spine.

The adjustable rod assembly preferably includes at least one bone connecting element, a first elongate member, a second elongate member and a locking element. The bone connecting element preferably is for attaching to the rib cage, pelvis or spine of a patient, including the vertebrae of a patient. The first elongate member preferably includes a first rod portion configured for coupling to one of the bone connecting elements and a first expansion portion, the first expansion portion further including a plurality of bore holes, preferably blind bore holes, in an outer surface. The second elongate member preferably includes a second rod portion configured for coupling to one of the bone connecting elements and a second expansion portion slideably movable with respect to the first expansion portion. The second expansion portion preferably further includes a plurality of through holes in an outer surface. The locking element preferably includes a pin configured to be insertable into at least one of each of the bore holes and the through holes to thereby couple the first and second elongate members together and fix or secure the length of the adjustable rod assembly. The bone connecting element preferably is rotationally adjustable about at least one of the first rod portion and the second rod portion. The first elongate member may be straight or have a lordotic or kyphotic curvature. Likewise, the second elongate member may be straight, or have a lordotic or kyphotic curvature. Alternatively, portions of the first and second elongate members may be straight while other portions are curved.

The first and second elongate members, or portions thereof, preferably are curved such that their outer surface defines the direction of the radius of curvature so as to form a lordotic curvature. The elongate members or portions thereof may also be relatively straight or form a kyphotic curvature. The first expansion and second expansion portions preferably are each curved and each preferably has the same radii of curvature. The radius of curvature of the first and second elongate members and/or the first and second expansion portions preferably is between about 200 mm to about 520 mm. The bone connecting elements may take on many forms and configurations, and may include, for example; hooks, including, for example, spinal hooks, lamina hooks, pedicle hooks, transverse processes hooks, spinal processes hooks, pelvic hooks, and S-hook members; clamp assemblies; screws, including, for example, pedicle screws, and pelvic screws. The clamp assembly may take many forms and configurations, such as, for example, a rib hook and a rib hook cap, a "C" clamp or other clamp configurations.

The adjustable rod assembly may form a system comprising a plurality of first elongate members of different sizes and shapes and a plurality of second elongate members of different sizes and shapes. The adjustable rod assembly system may further comprise multiple bone connecting elements including at least one clamp for attachment to a patient's rib, at least one hook for attachment to a patient's vertebra, preferably the lamina of the vertebra, and/or at least one hook for attachment to a patient's pelvis area.

A method of implanting an adjustable rod assembly for correcting or straightening a human spine is also disclosed. The method may include the steps of inserting a first bone connecting element through a first opening to a first location in a patient, coupling the first bone connecting element to bone at the first location, inserting a second bone connecting element through a second opening to a second location in a patient, coupling the second bone connecting element to bone at the second location, inserting a first elongate member through the first opening, coupling the first elongate member to the first bone connecting element, inserting a second elongate member through the second opening, coupling the second elongate member to the second bone connecting element; and coupling the elongate members together.

The method may further comprise the steps of creating a third opening at a third location and inserting a coupler or locking element through the third opening to couple the elongate members together. The first elongate member may have a first rod portion and the method may further comprise the steps of coupling the first bone connecting element to the first rod portion, and angularly adjusting the first bone connecting element relative to the first rod portion. The method may further comprise the step of fixing the angular orientation of the first bone connecting element with respect to the first rod portion.

Other arrangements, structures, features, embodiments, aspects, instrumentalities, methods and constructions of the adjustable rod assembly will be evident to those skilled in the art upon review of the detailed description, and the present invention should not be limited to the summary, and/or preferred embodiments shown and described.

BRIEF DESCRIPTION OF THE SEVERAL VIEWS OF THE DRAWINGS

The foregoing summary, as well as the following detailed description of preferred embodiments of the application, will be better understood when read in conjunction with the appended drawings. For the purposes of illustrating the adjustable rod assembly of the present application, drawings of preferred embodiments are shown. It should be understood, however, that the application is not limited to the precise arrangements, structures, features, embodiments, aspects, methods and instrumentalities shown, and the arrangements; structures, features, embodiments, aspects, methods and instrumentalities shown may be used singularly or in combination with other arrangements, structures, features, embodiments, aspects, methods and instrumentalities. In the drawings:

FIG. 17A illustrates a cross-sectional view of the transverse rib hook of FIG. 17 along line 17A-17A; and FIG. 17B illustrates a perspective back view of the transverse rib hook of FIG. 12.

DETAILED DESCRIPTION OF THE INVENTION

Figure 1:
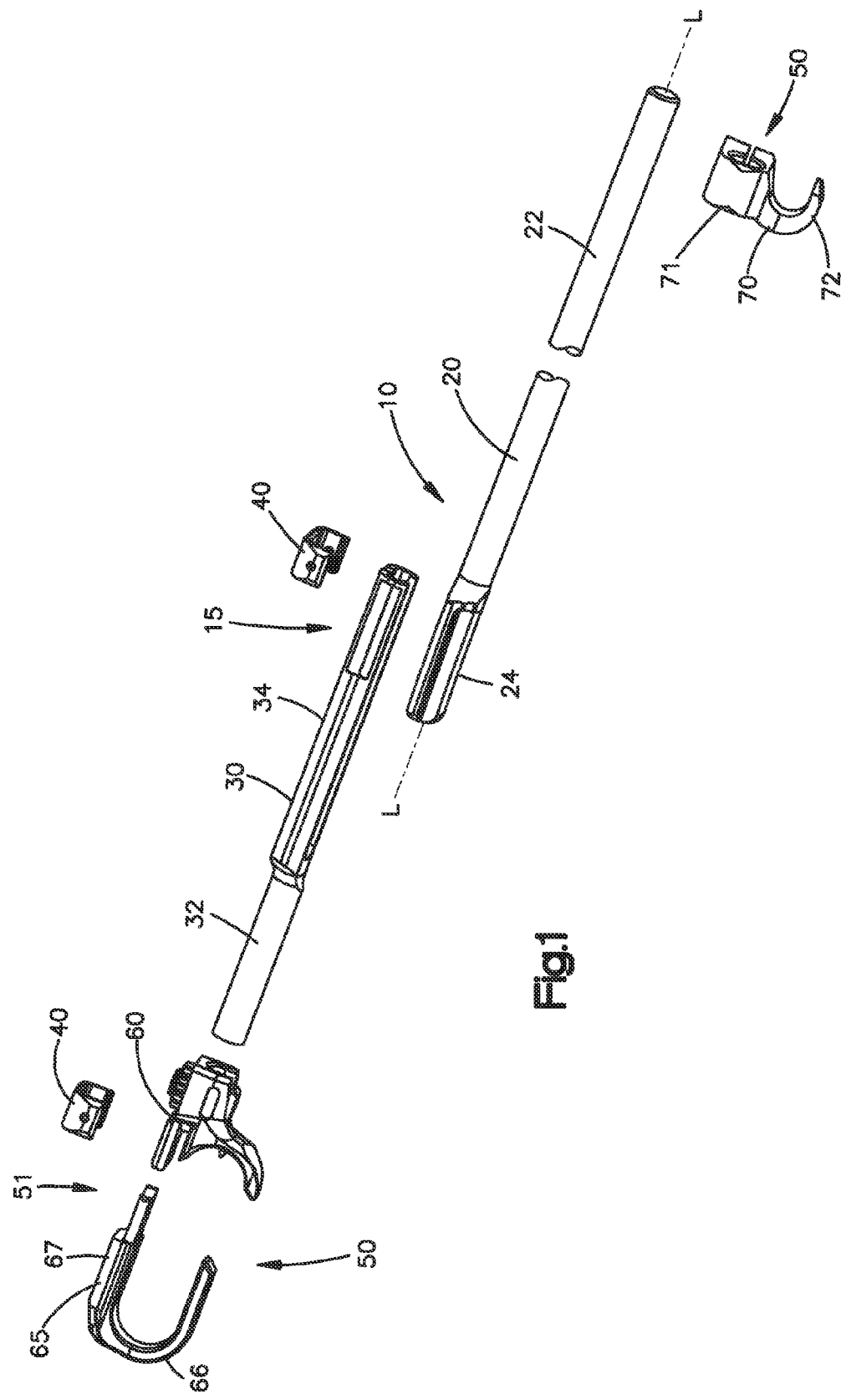
FIG. 1 illustrates an exploded perspective view of an adjustable rod assembly in accordance with a first preferred embodiment of the present invention.

Certain terminology is used in the following description for convenience only and is not limiting. The words "right", "left", "lower", "upper", "top" and "bottom" designate directions in the drawings to which reference is made. The words "inner", "inwardly" or "distally" and "outer", "outwardly" or "proximally" refer to directions toward and away from, respectively, the geometric center of the adjustable rod assembly and related parts thereof, or the patient. The words, "anterior", "posterior", "superior," "inferior", "lateral" and "medial" and related words and/or phrases designate preferred positions and orientations in the human body to which reference is made and are not meant to be limiting. The terminology includes the above-listed words, derivatives thereof and words of similar import.

In reference to FIGS. 1-5, and 15, an adjustable rod assembly 10 is provided that includes one or more adjusting assemblies 15 and one or more bone connecting elements 50. U.S. Pat. No. 5,092,889 and U.S. Pat. No. 5,261,908 describe, show and disclose adjustable rod assemblies similar to those described herein which are for use to correct and alleviate similar conditions, the contents of U.S. Pat. Nos. 5,092,889 and 5,261,908 are incorporated in their entirety herein by reference.

The adjusting assemblies 15 in FIGS. 1-9 and 15 may include a first elongate member or distal extension 20, a second elongate member or proximal extension 30, and a locking element 40. The first and second elongate members 20, 30 and the locking element 40 can be formed from a number of biocompatible materials, such as, for example, titanium, stainless steel, titanium alloy, cobalt-chrome, composites, ceramics, PEEK, or other polymers. These materials are not limiting and the elongate members 20, 30 and the locking element 40 may be constructed of nearly any biocompatible material that is able to take on the desired shape and withstand the normal operating conditions (e.g., the environmental and physical property requirements) of the adjusting assemblies 15.

Figure 6:
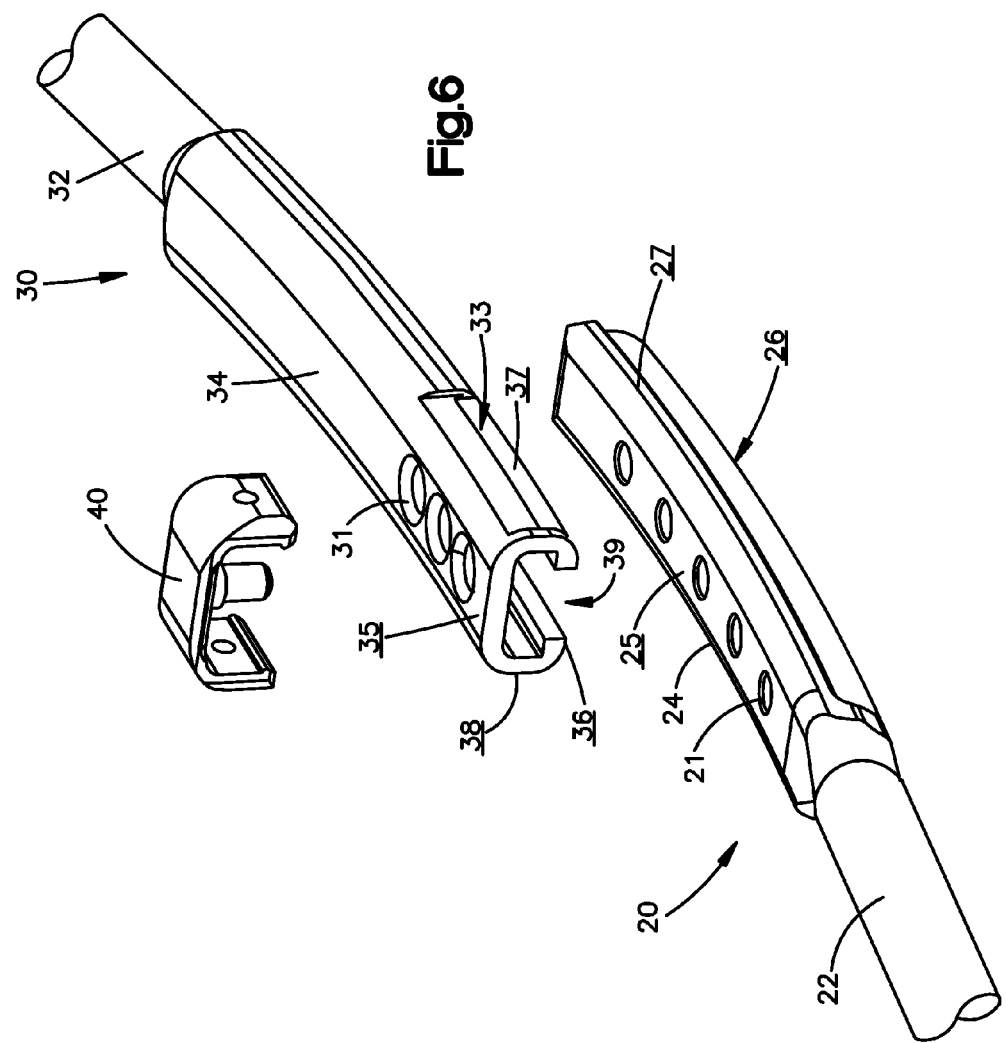
FIG. 6 illustrates an exploded perspective view of a first embodiment of the connecting assembly of the adjustable rod assembly.
Figure 7:
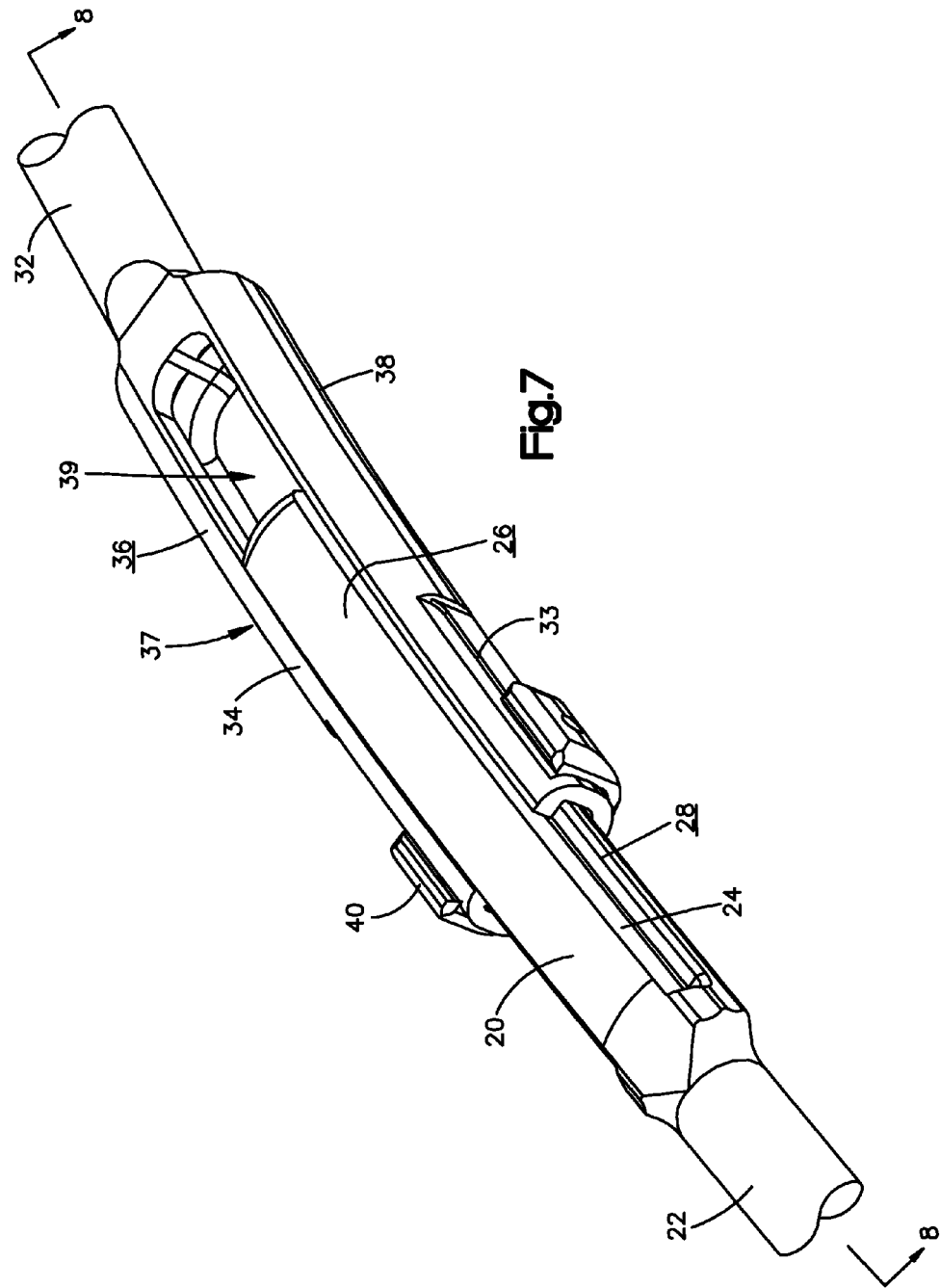
FIG. 7 illustrates a bottom view of the assembled connecting assembly of FIG. 6.
Figure 8:
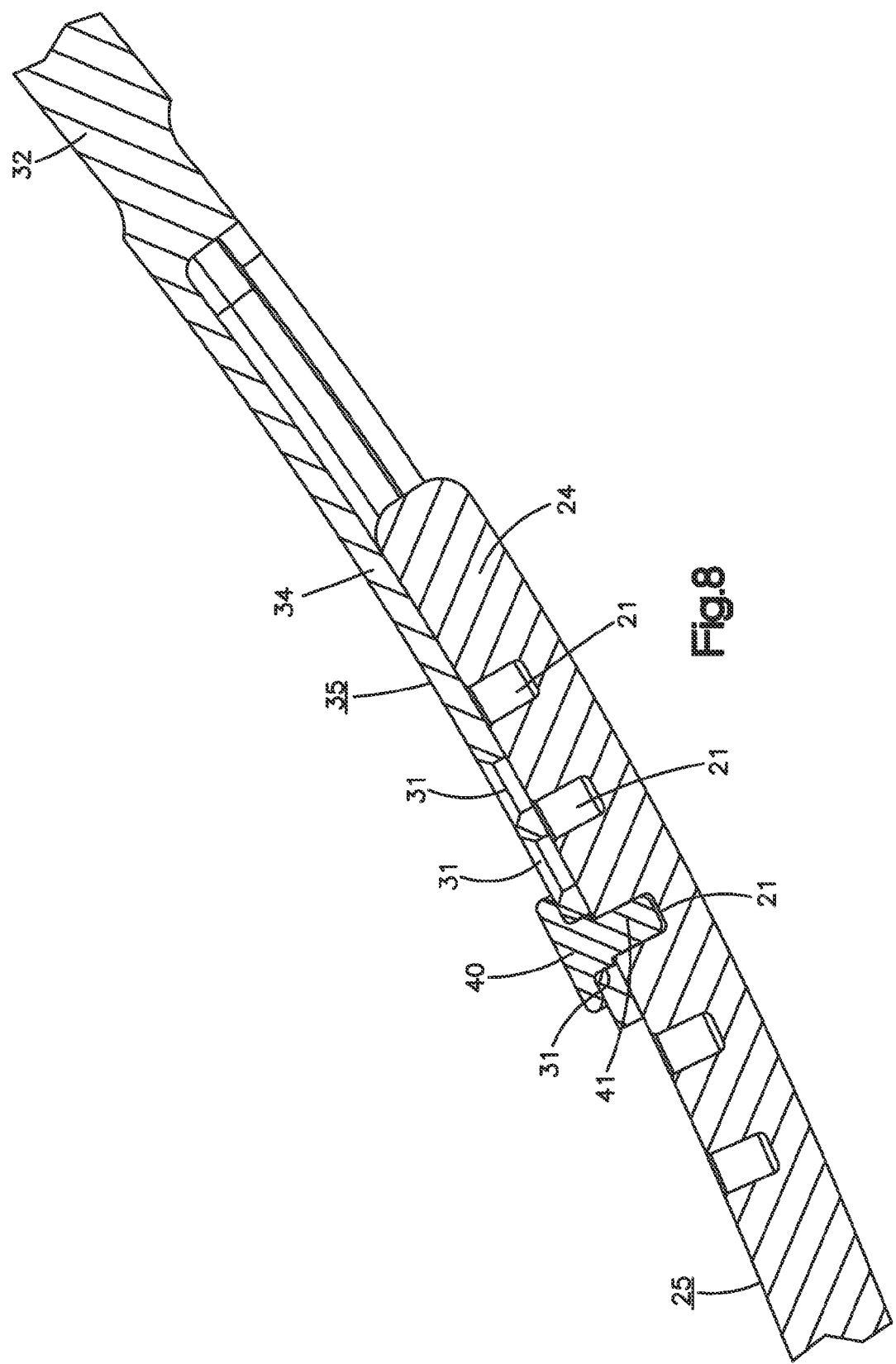
FIG. 8 illustrates a cross-sectional view of the assembled connecting assembly of FIG. 7 along line 8-8.
Figure 9:
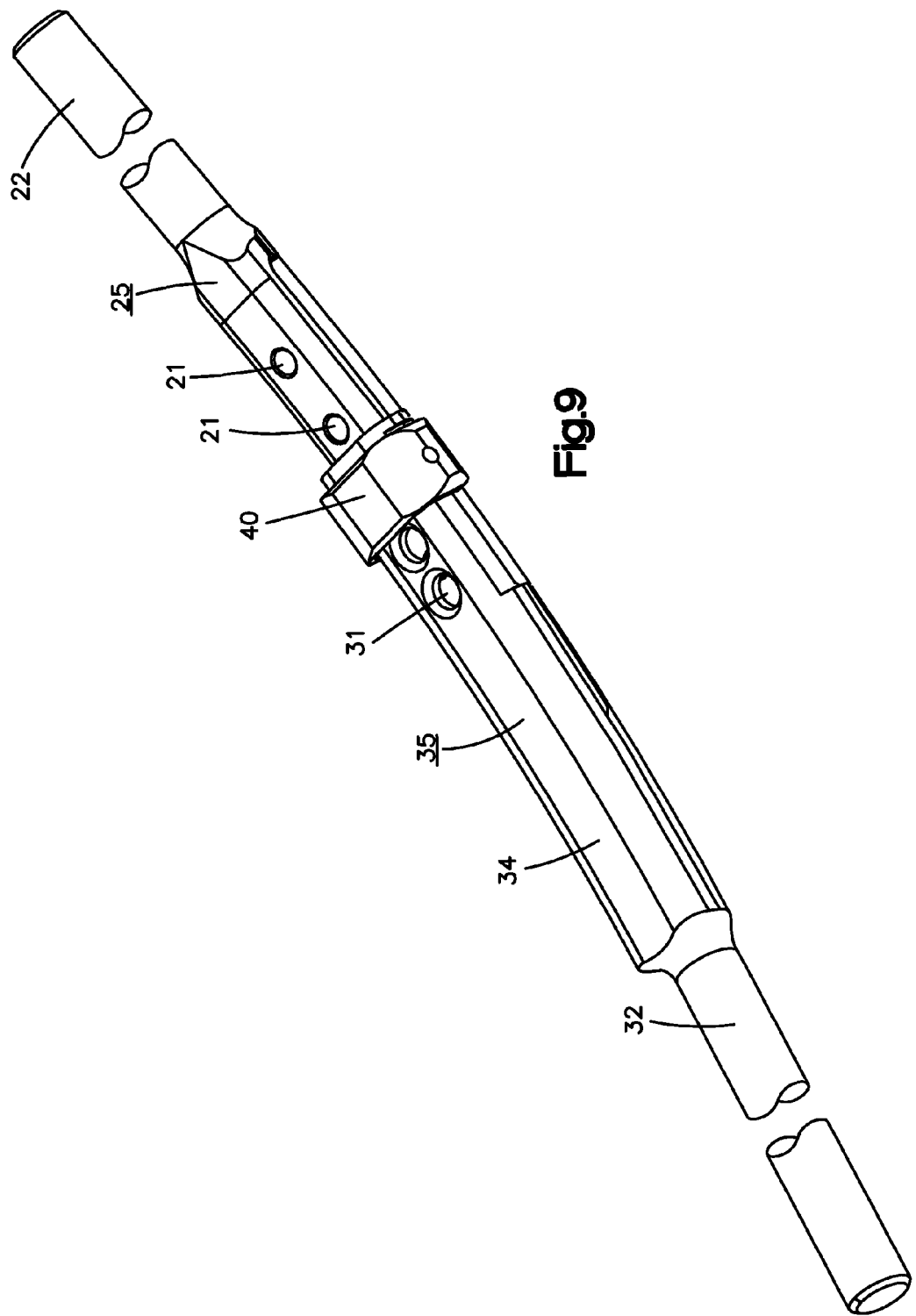
FIG. 9 illustrates a perspective view of the connecting assembly of the adjustable rod assembly of FIG. 6.

Referring to FIGS. 6-9, the first elongate member 20 of the adjusting assembly 15 includes a male expansion portion 24 and a first rod portion 22 configured for coupling to one or more first bone connecting elements 50. The male expansion portion 24 preferably includes an outer surface 25, an inner surface 26, and a pair of side surfaces 27, 28 that combine to form a T-bar shape when the male expansion portion 24 is viewed in cross-section. Disposed through the outer surface 25 of the male expansion portion 24 is a plurality of blind bore holes 21, as is best shown in FIG. 6. Preferably the blind bores 21 do not extend all the way through the male expansion portion 24 from the outer surface 25 to the inner surface 26.

The second elongate member 30 includes a female expansion portion 34 and a second rod portion 32 configured for coupling to one or more second bone connecting elements 50. The female expansion portion 34 is configured to slideably translate with respect to the male expansion portion 24. The female expansion portion 34 preferably includes an outer surface 35, a pair of side surfaces 37, 38 and an inner surface 36 with an opening 39 that preferably form a sleeve like member with a "C" shape when the female expansion portion 34 is viewed in cross-section. The sleeve like expansion portion 34 has a channel to receive the male expansion portion 24. Disposed through the outer surface 35 of the female expansion portion 34 is a plurality of complementary through holes 31.

While the surfaces of male extension portion 24 and the female extension portion 34 have been shown and described as forming a T-Bar shape and a C-shaped channel, other shapes and geometries may be utilized for the male extension portion 24, such as, for example, an I-beam shape, and for the female extension portion 34, such as, for example, an I-shaped or T-shaped channel. The first elongate member 20 preferably translates or slides relative to the second elongate member 30, preferably while limiting or preventing rotation of elongate members 20, 30 with respect to each other. The shape and interaction between the two members 20, 30 preferably prevents or resists relative rotation between the two members. Preferably the male expansion portion 24 slides and telescopes within the female expansion portion 34, however, it is contemplated that the elongate members can slide and telescope in a side by side manner as well. The sliding action between first elongate member 20 and the second elongate member 30 permits the surgeon to adjust the length of the adjustable rod assembly 10 before or during the procedure.

Figure 10:
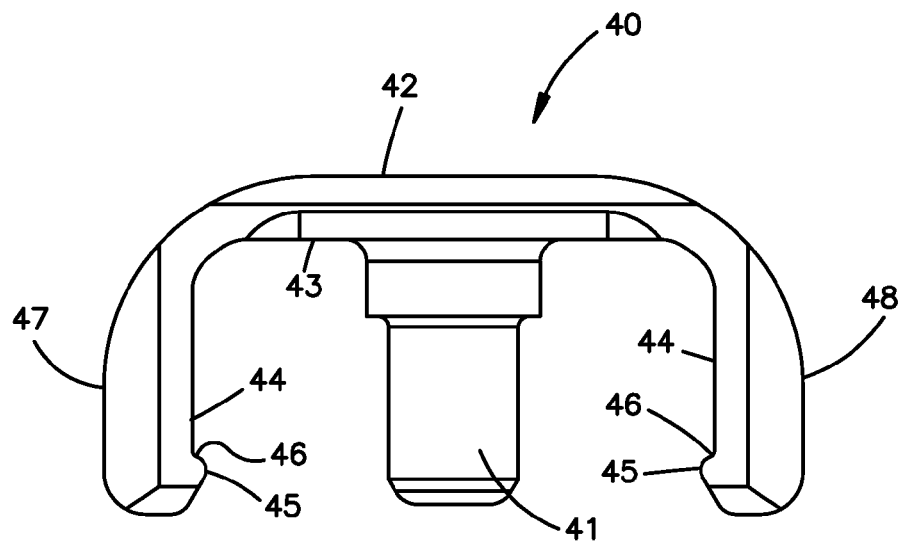
FIG. 10 illustrates a side elevational view of a locking element for use in the adjustable rod assembly.

Referring to FIG. 10, the locking element or coupler 40 preferably includes a substantially flat outer surface 42, and a pair of side surfaces 47, 48, and is shaped as a C-clamp having a prong 41 protruding from its inner surface 43 in the same direction as the side surfaces 47, 48. The prong 41 is configured to be insertable in the through holes 31 and the blind bore holes 21 to prevent relative motion between first and second elongated members 20, 30. The bottom inside surface 44 of the locking element 40 has a small projection 45 forming a shoulder 46 for engaging and snapping onto a ledge 33 formed in the side surfaces 37, 38 of the female extension 24. The locking element 40 is preferably elastically deflectable so that the side walls 37, 38 can deflect and expand so that projections 45 can extend down over ledge 33. In this manner, the locking element 40 is snap fitted and attached to the elongate member 30 as the projections 45 engage and couple to the ledge 33. The sliding action between the elongate members 20, 30 permits the surgeon to adjust the length of the adjustable rod assembly 10 while the locking element 40 allows a surgeon to secure or fix the length of the adjustable rod assembly at its desired length.

Figure 2:
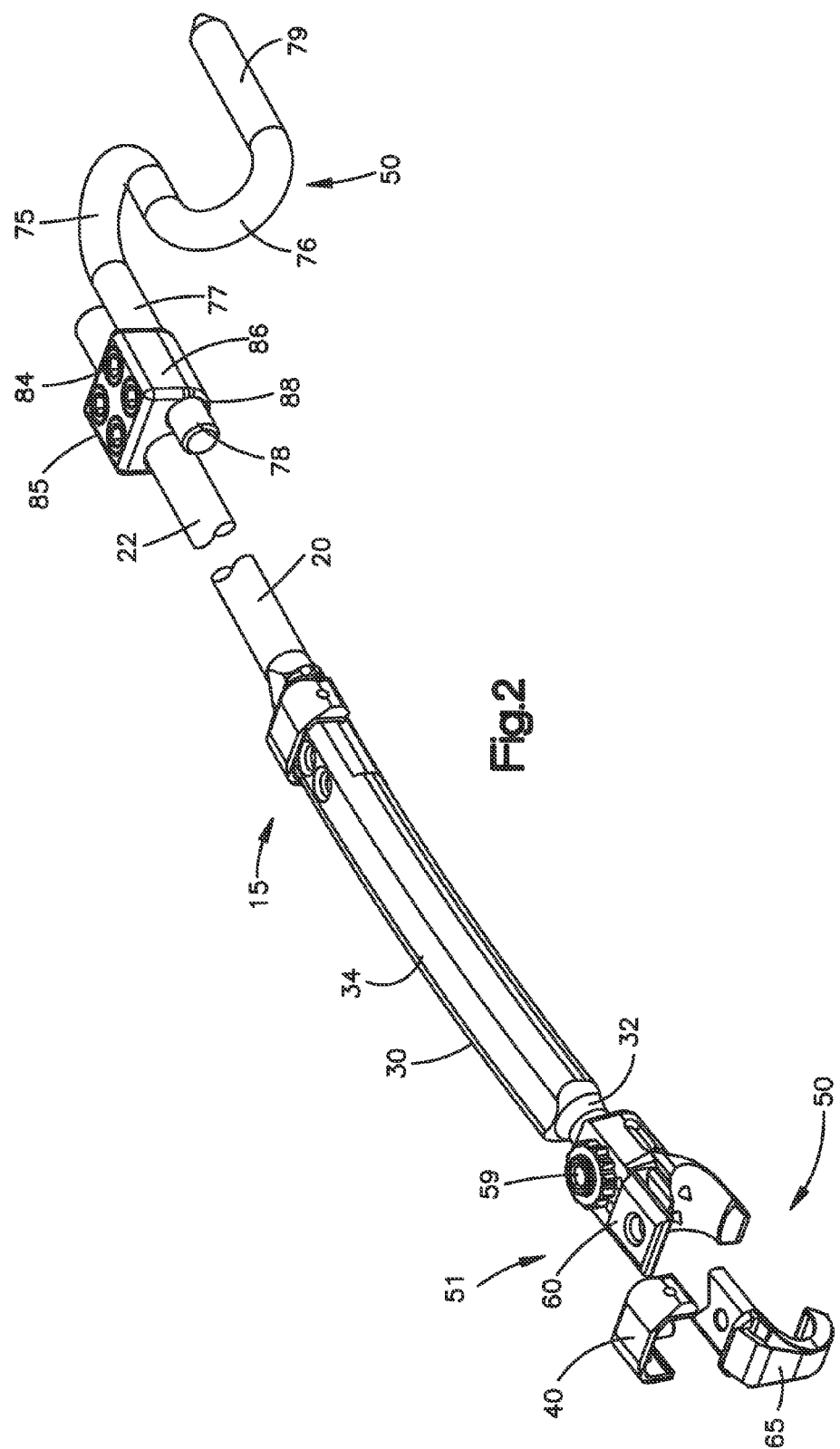
FIG. 2 illustrates an exploded perspective view of an adjustable rod assembly in accordance with a second preferred embodiment of the present invention.
Figure 3:
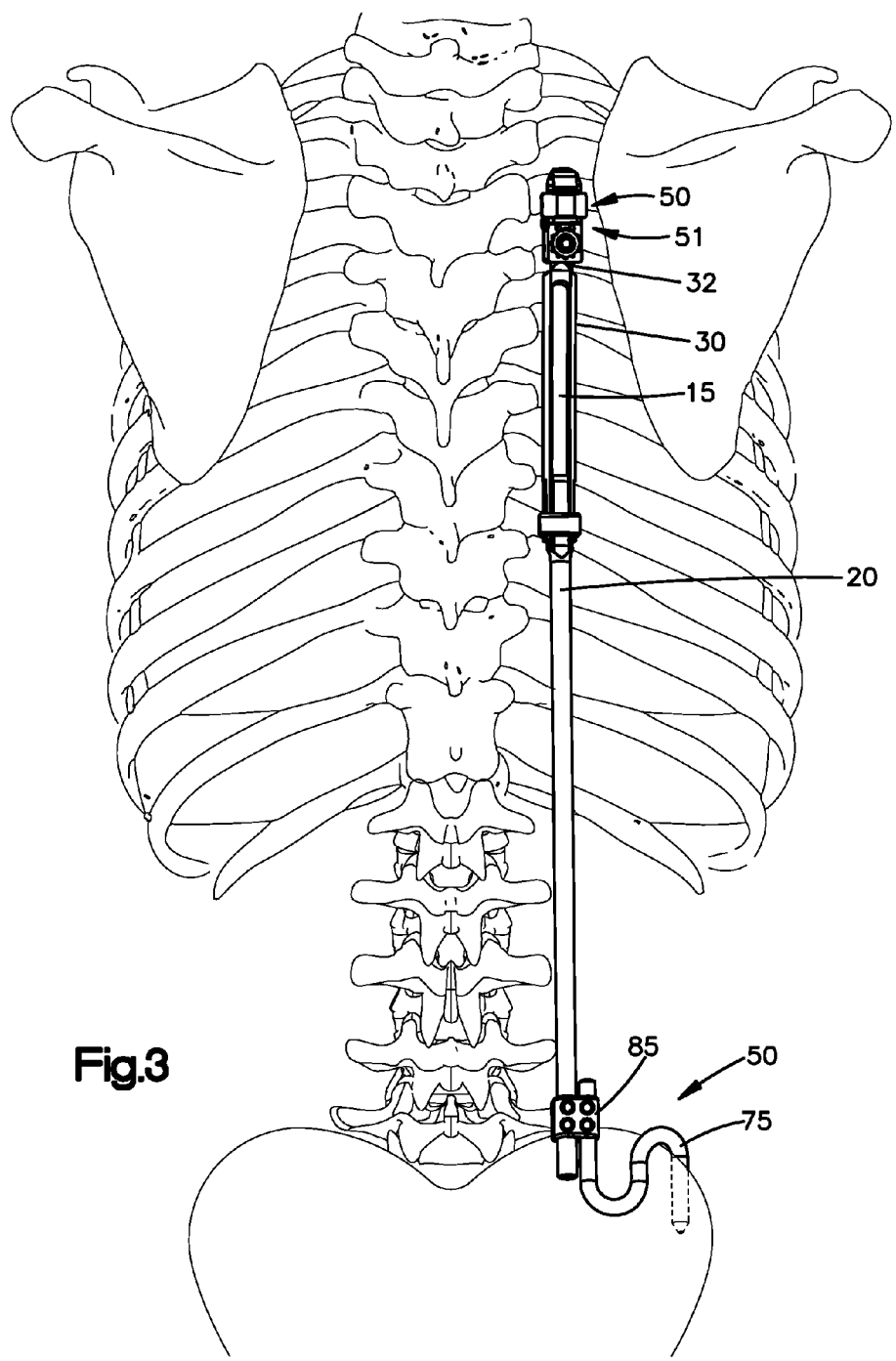
FIG. 3 illustrates a top view of the adjustable rod assembly of FIG. 2 connected to the rib cage and pelvis of a patient.

The elongate members 20, 30 in the adjustable rod assembly 10 of FIG. 1 are substantially straight while the elongate members 20, 30 of the adjustable rod assembly 10 of FIGS. 2-5 and 15 are slightly curved, having a kyphotic curvature when attached to bone. In this regard, the ends of the curved elongate members in the embodiments of FIGS. 2-5 and 15 are bent inward toward the inner surfaces 26, 36 of the elongate members 20, 30. When the adjustable rod assembly is attached to the posterior side of the patient as shown in FIG. 3 the radius of curvature of the elongated member is toward the inner surfaces 26, 36 of the elongated members forming and defining a kyphotic curvature. In the adjusting assemblies 15 of FIGS. 6-9 the radius of curvature of the elongated members is toward the outer surfaces 25, 35 of the elongate members forming and defining a lordotic curvature when the adjustable rod assembly 10 is attached to a patient. The ends of the curved elongate members 20, 30 in FIGS. 6-9 are bent toward the outer surface, i.e., in the embodiment of FIGS. 6-7 toward the surfaces 25, 35 that contain the bores 21 and holes 31, of the elongate members 20, 30 to form the lordotic curvature.

The entire elongate members 20, 30 may be straight, curved or portions of the elongate members 20, 30 may be curved and/or straight. For example, the rod portions 22, 32 may be straight while the extension portions 24, 34 may be curved (lordotic or kyphotic curvature or combination) or vice versa, the extension portions 24, 34 may be straight while the rod portions 22, 32 are curved. Other regions of the elongate members, or partial portions of the rod portions and/or extension portions may be a combination of curved and straight.

The adjustable rod assembly 10 preferably has one or more bone connecting elements. The bone connecting elements may take on many forms and configurations, and may include, for example; hooks, including, for example, spinal hooks, lamina hooks, pedicle hooks, transverse process hooks, spinous process hooks, spinal hooks, pelvic hooks, and S-hook members; clamp assemblies; screws, including, for example, pedicle screws, and pelvic screws. The clamp assembly may take many forms and configurations, such as, for example, a rib hook and a rib hook cap, a "C" clamp or other clamp configurations. The adjustable rod assembly in FIGS. 1-5 have two bone connecting elements 50, one attached to the rod portion 22 of the first elongate member 20 and one connected to the rod portion 32 of the second elongated member 30. The adjustable rod assembly of FIG. 15 has three bone connecting elements 50, one (not shown) connected to the rod portion 22, one connected to the proximal end of the rod portion 32 and one connected to a transverse bar 90.

The bone connecting elements 50 preferably are angularly adjustable with respect to the elongate members 20, 30 by rotating the connecting elements 50 about and with respect to the elongate elements. The angular adjustability of the elongate elements is permitted and facilitated by the preferred cylindrical shape of the rod portions 22, 32 of the elongate members interacting with openings, preferably U-shaped openings, in the bone connecting elements 50. While the preferred shape of the rod portions have been shown and described as cylindrical it will be appreciated that other shapes and configurations that will provide the preferred angular adjustability of the bone connecting element 50 with respect to the adjustable assembly 15 are contemplated. After the bone connecting elements 50 are oriented as desired with respect to the respective elongate member, the position of the connecting element 50 may be fixed or secured with respect to the elongate element via a locking mechanism.

Figure 11:
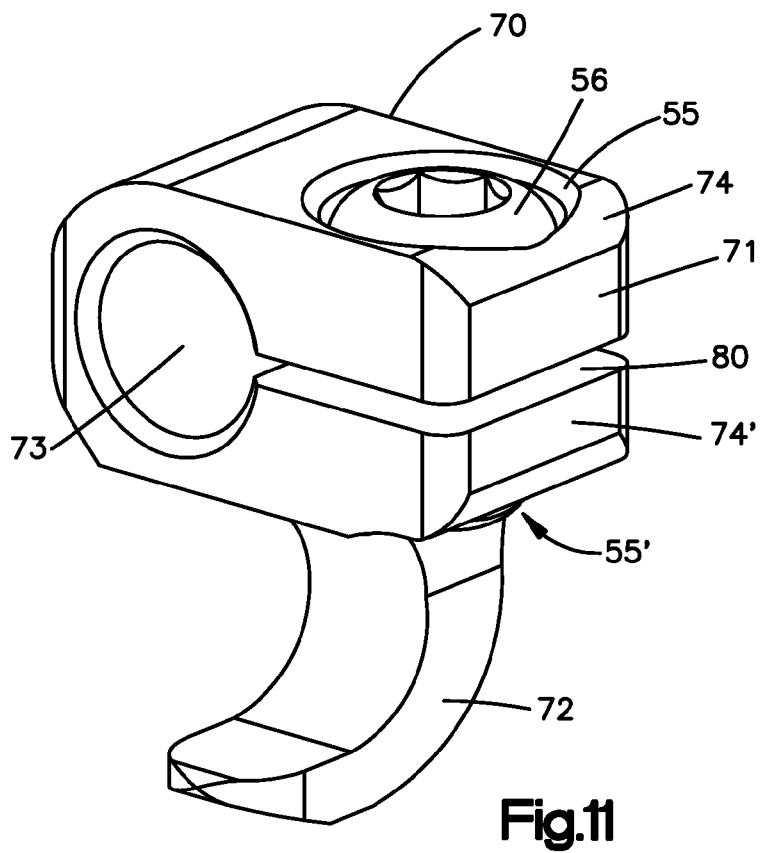
FIG. 11 illustrates a perspective view of a lamina hook of the adjustable rod assembly of FIG. 1.

The bone connecting elements 50 in the embodiment of FIG. 1 are different at each end of the adjustable rod assembly 10. The bone connecting element 50 connected to the rod portion 22 of the first elongate member 20 is in the form of a lamina hook 70, shown in FIG. 11. Lamina hook 70 may be formed as a single monolithic piece or multi-piece hook with a locking screw 56 for fixing the position of the hook 70 along the length of the elongate member, such as, for example, elongate member 20 in the embodiment of FIG. 1. The lamina hook 70 includes a clamping portion 71 and a hook portion 72. The hook portion 72 is configured, sized and oriented preferably to engage the lamina portion of the vertebrae but may be configured, sized and oriented to attach to other parts of the vertebrae, spine, rib, pelvis or other bones.

The clamping portion 71 preferably is formed as a C-clamp having a through bore 73 and two leg portions 74, 74'. Each leg portion 74, 74' has a screw hole 55, 55' extending there through to receive locking screw 56. The screw hole 55' preferably has inner threads (not shown), preferably only on one leg, for example, leg 74', that mate with the threads on the locking screw 56 so that as the screw 56 is tightened, the gap 80 between the legs 74, 74' decreases so that the size of through bore 73 decreases to provide a clamping force on the rod portion 22 to fix the position of the lamina hook 70 on the elongate member 20. The position of the lamina hook 70 along the length of the elongate member, and preferably along the length of the rod portion 22, is adjustable by the surgeon. In addition, lamina hook 70 preferably can be rotated about the longitudinal axis L of the elongate member 20 to adjust the angular orientation of the lamina hook 70 with respect to the elongate member 20 and the adjustable rod assembly 10. The screw hole 55, 55' preferably is orientated perpendicular to the through bore 73, but other angular relationships are contemplated.

The bone connecting element 50 connected to the second elongate element 30 in the embodiment of the adjustable rod assembly 10 of FIG. 1 is in the form of a clamping assembly 51 adapted for attachment to the rib of a patient. While the clamping assembly 51 is shown and described as attaching to a rib, it can be appreciated that the clamping assembly can attach to other locations, parts and bones. The clamping assembly 51 may comprise two or more pieces and as little as a single piece.

Figure 12:
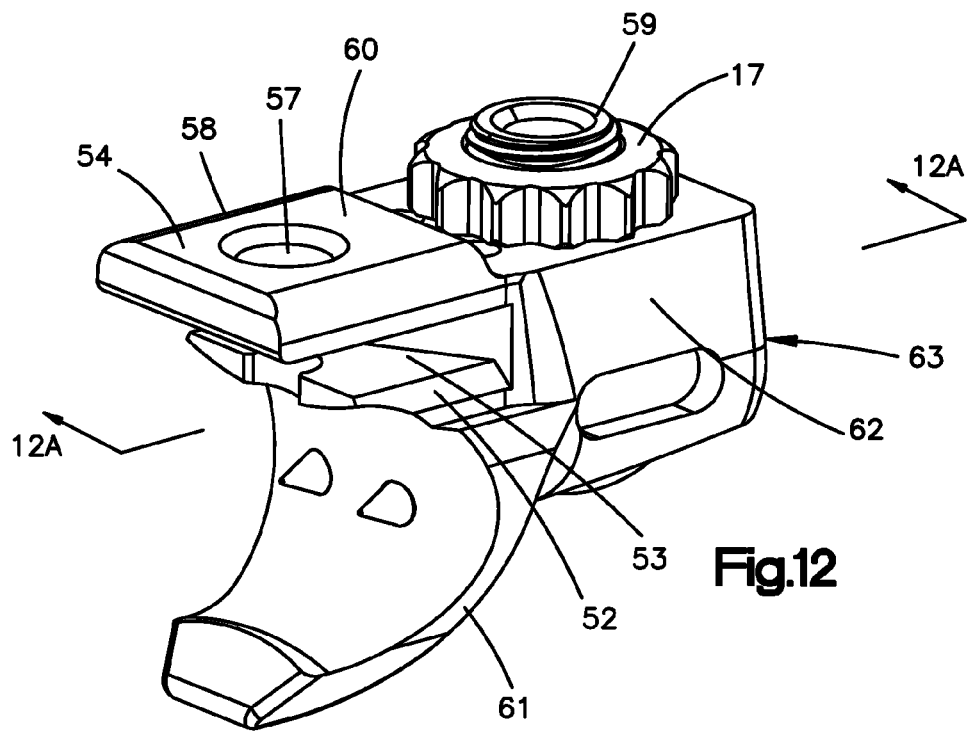
FIG. 12 illustrates a perspective side view of a rib hook of the bone clamping assembly of FIGS. 1-5.
Figure 12A:
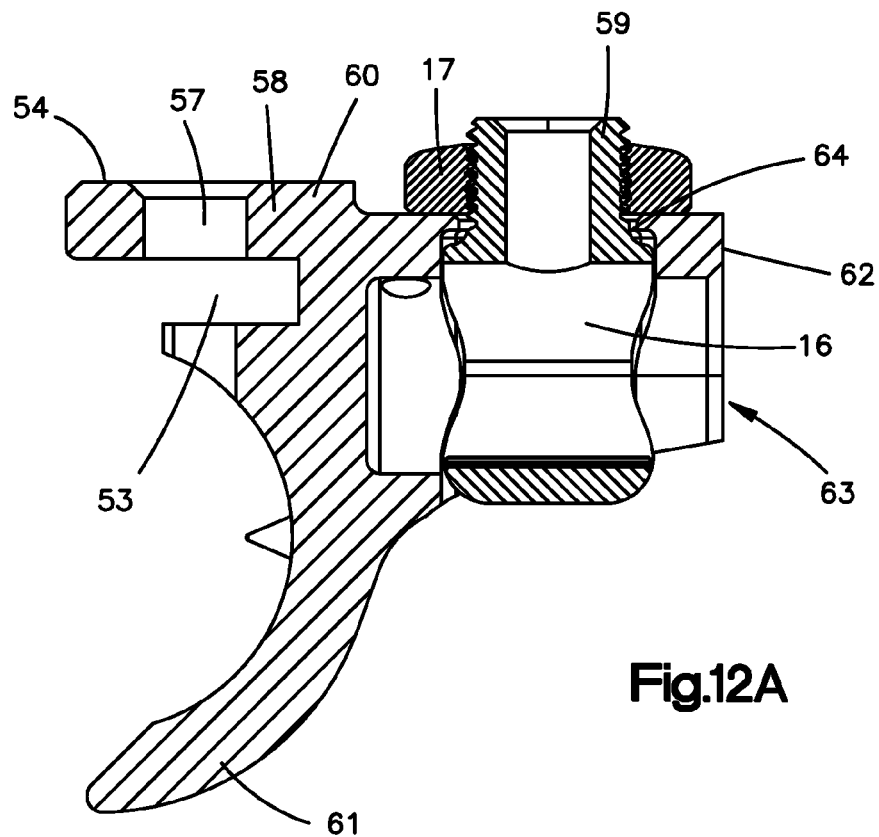
FIG. 12A illustrates a cross-sectional view of the rib hook of FIG. 12 along line 12A-12A.
Figure 12B:
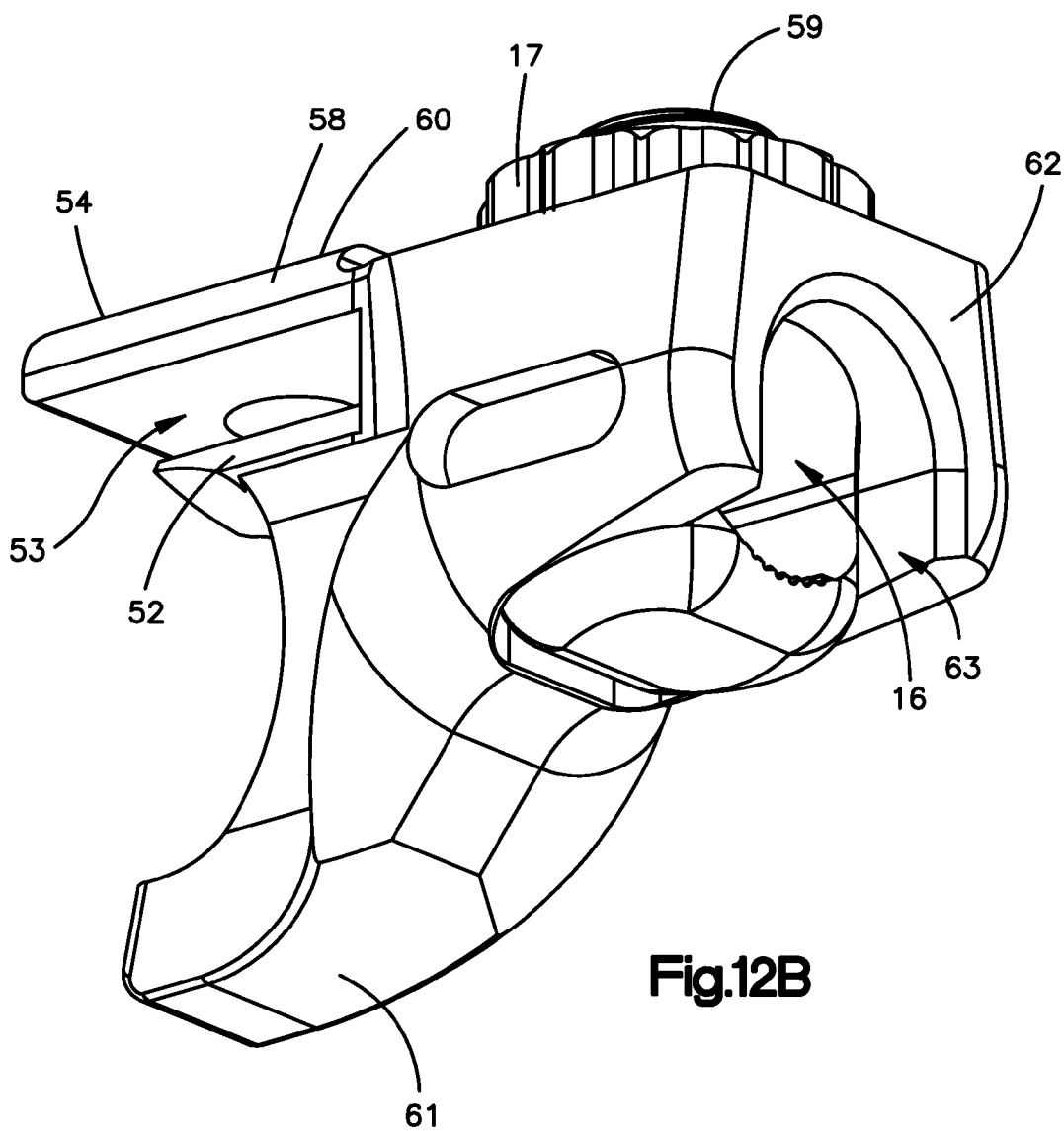
FIG. 12B illustrates a perspective back view of the rib hook of FIG. 12.

Clamping assembly 51 in FIGS. 1-5 includes a rib hook 60, a rib hook cap 65 and locking element 40 for connecting the rib hook 60 to the rib hook cap 65. Rib hook 60 as shown in FIGS. 12-12B includes a hook portion 61 and a connecting portion or body 62. Hook portion 61 is configured, sized and oriented preferably to fit at least partially around the rib of a patient. Connecting portion 62 includes an opening 63 to receive the rod portion 22, 32 of the elongate members 20, 30. The rod portion is inserted in the opening 63 and preferably the angular orientation of the rib hook 60 can be adjusted with respect to the elongate members 20, 30. That is, the shape of opening 63 permits the preferred cylindrically shaped rod portion 22, 32 to rotate in the opening about longitudinal axis L. The opening 63 in the embodiment of FIGS. 12-12B is preferably U-shaped as shown, although other shapes are contemplated. The opening 63 may be open at the back and bottom as shown in FIG. 12B, or the opening 63 in the back of body 62 may be substantially cylindrically shaped. The rod portion 22, 32 may be locked and fixed with respect to the clamp assembly 51 as explained below.

The connecting portion 62 of the rib hook 60 further includes an opening 64 generally transverse to and preferably orthogonal to the opening 63. The opening 64 preferably intersects the opening 63 and a locking element 59 interacts and fits within the opening 64 to lock the elongate members 20, 30 with respect to the rib hook 60. A nut 17 preferably has internal threads that interact with threads formed on the locking element 59 to move the locking element 59 with respect to the body 62 to lock and fix the position of the rod portion of the elongate members. The locking element 59 includes an opening 16 sized to permit the rod portion of the elongate members to pass there through. To insert the rod portion of the elongate member in the opening 63 of the body 62, the opening 16 of the locking element overlaps and/or is aligned with opening 63 to permit the rod to pass through the opening 16. To lock the angular orientation and position of the rib hook 60 with respect to the elongate members the surgeon turns the nut 17 to move the locking element 59 so that the opening 16 of the locking element 59 shifts within the body 62 and clamps the rod portion in the body 62 to fix the position of rib hook 60. The surgeon can adjust the angular orientation of the rib hook 60 on the elongate member by rotating the rib hook on the elongate member and thereafter operating the nut 17 to fix the angular orientation of the rib hook 60 with respect to the elongate member.

Alternatively, a set screw (not shown) may be fitted within the opening 64 to lock and fix the position of the rod portion with respect to the rib hook 60. the set screw would be turned to move the set screw so that the end of the set screw abuts against and clamps the rod portion in the opening 63. The set screw and opening 64 preferably would have interacting threads to couple the set screw to the rib hook 60 and to control its movement in the opening 64.

The connecting portion or body 62 further includes the cap receiving portion 58 having an extension 54, a hole 57 through the extension 54, and a slot 53 below the extension 54 and above the hook portion 61. A locking element 40, as will be described below, interacts with the cap receiving portion 58 and ledge 52 to connect the rib hook cap 65 to the rib hook 60.

Figure 13:
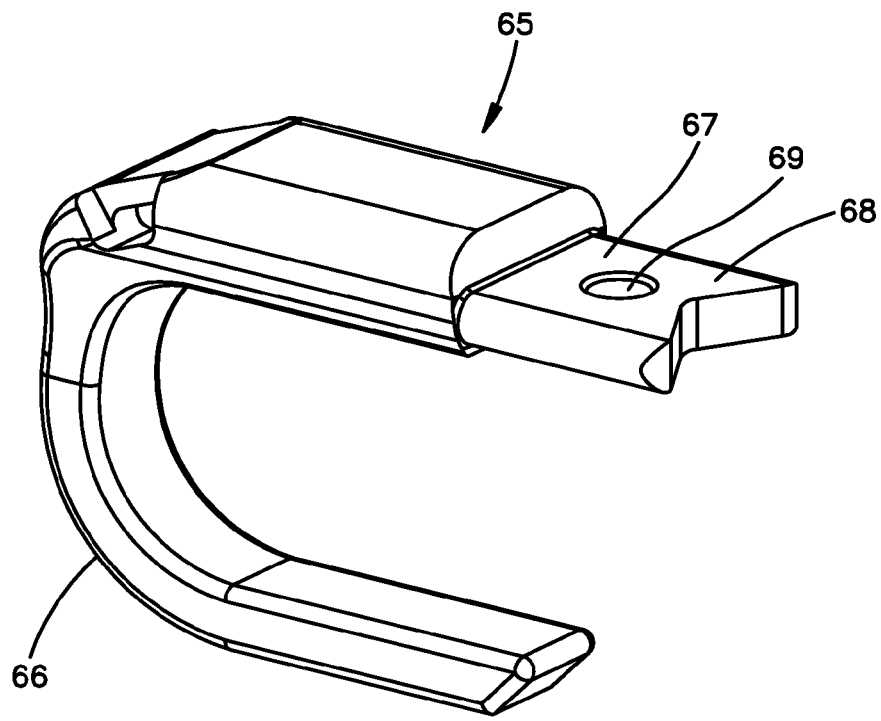
FIG. 13 illustrates a perspective view of the rib hook cap of the bone clamping assembly of FIGS. 1-4.
Figure 14:
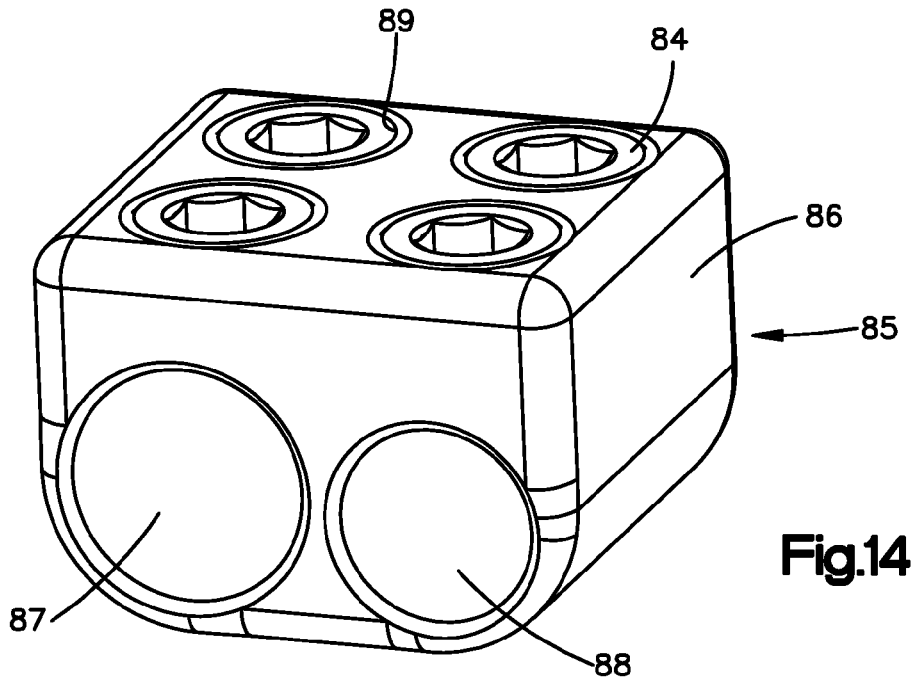
FIG. 14 illustrates a perspective view of a parallel connector of the adjustable rod assembly of FIG. 2.

Rib hook cap 65 as shown in FIG. 13 has a hook portion 66 and a connecting portion 67. The connecting portion 67 has an extension 68 that is received in the slot 53 in the connecting portion 62. One or more aligned but spaced apart holes 69 are provided in the connecting portion 67. The extension 68 is inserted into the slot 53 and one of the holes 69 is aligned with hole 57 and the locking element 40 is clipped over extension 54 and extension 68 so that the prong 41 extends down through the aligned holes 69 and 57. The side walls 47, 48 of the locking clip 40 expand and deflect so that the projections 45 snap over ledge 52 formed in the connecting portion 62. The locking element 40 thereby preferably fixes the rib hook cap 65 to the rib hook 60. The hook portion 61 of the rib hook 60 and the hook portion 66 of the rib hook cap preferably extend about and capture the patient's rib to act as a bone attachment anchor for the adjustable rod assembly 10. Because of the multiple holes 69, the size of the space created by the rib hook 60 and rib hook cap 65 can be adjusted to fit different size ribs. Alternatively and additionally, different size rib hook caps 65 may be provided, and/or different size rib hooks 60 may be provided in order to provide different size bone connecting elements 50 for attachment to a multitude of different size ribs.

FIG. 2 shows an alternative second preferred embodiment of adjustable rod assembly 10. The bone connecting element 50 attached to one end of the assembly is the same as the clamping assembly 51 described in FIG. 1. The bone connecting element 50 attached to the other end of the adjustable rod assembly 10 comprises a S-hook connector 75. The S-hook connector 75 has a hook portion 76 and a connecting portion 77. The hook portion 76 is shaped similar to an "S"-shape and preferably is configured and oriented as a pelvic hook and preferably is configured and oriented to slip over the top of the pelvis in the area of the iliac crest as shown in FIG. 3. The end 79 of the hook portion 76 is not in the same plane as the middle portion or the end of the hook portion 76 that is connected to the connecting portion 77. In this manner, end 79 extends along the anterior side of the iliac crest while the arch or curved section of the hook portion 76 extends up and over the iliac crest. The remainder of the hook portion 76 extends down along the posterior side of the iliac crest and back up toward the rib cage. The connecting portion 77 is preferably a generally straight rod section 78 that extends from the hook portion 76. Although rod section 78 is shown as generally straight it may also be curved and/or a combination of straight and curved sections. S-hook connector 75 may come in different sizes and lengths. The hook portion 76 may come in different sizes to fit a variety of pelvis and the rod section 78 may come in a multitude of different lengths to accommodate different size adjustable rod assemblies 10, for use in a variety of different patients.

The S-hook connector 75 is connected to the rod portion 32 of the elongate member 30 by parallel rod connector 85. Parallel rod connector 85 has a body 86 with two parallel channels 87, 88 extending through the body 86 and one or more openings 89 intersecting each of channels 87, 88. In the embodiment of FIG. 2, two openings 89 intersect channel 87 and two openings 89 intersect channel 88. The openings 89 are preferably threaded and receive locking screws 84. The two channels 87, 88 may be the same size and/or diameter or may be a different size. The rod section 78 of the S-hook connector 75 may be inserted into and through one of the channels, such as, for example, channel 88, while the rod portion 22, 32 of the elongate members 20, 30 may be inserted through the other channel, such as, for example, channel 87. The locking screws 84 are tightened to fix the position and angular orientation of the S-hook connector 75 with respect to the parallel connector 85, and the position and orientation of the parallel connector 85 with respect to the elongate members.

While the embodiment of the adjustable rod assembly 10 in FIGS. 2 and 3 uses parallel connector 85, an in-line connector (not shown) that has one channel, for example, channel 87, may also be used. In-line connector has one or more, and preferably two or more openings intersecting the channel for receipt of locking screws 84. The rod section 78 of the S-hook connector 75 is inserted in the first end of the channel 87 of the in-line connector and fixed by tightening the locking screw 84 while the rod portion of the elongate member is inserted in the second end of the channel 87 and fixed by tightening locking screw 84 to attach the S-hook connector 75 to the adjustable rod assembly 10.

Figure 4:
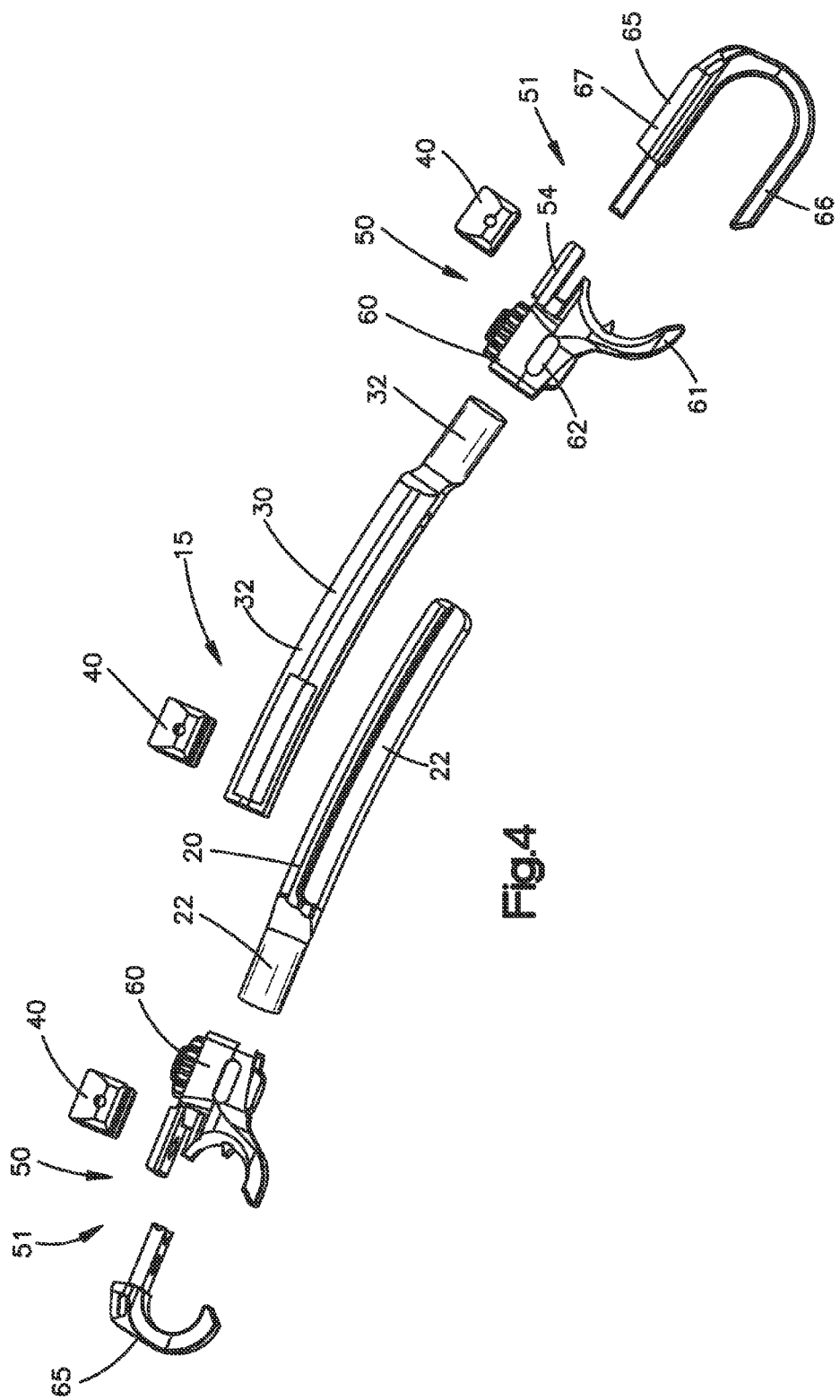
FIG. 4 illustrates an exploded side view of an adjustable rod assembly in accordance with a third preferred embodiment of the present invention.
Figure 5:
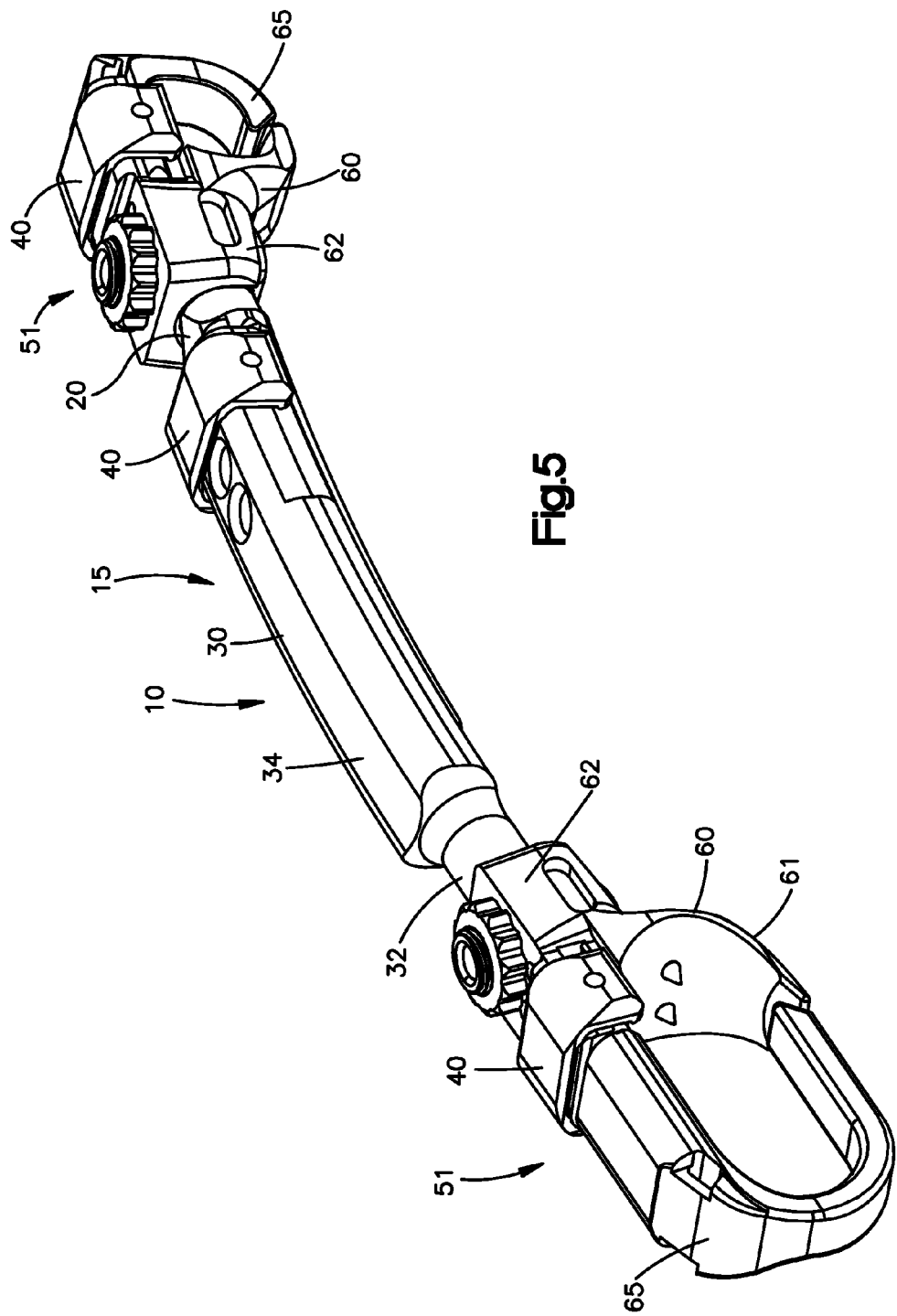
FIG. 5 illustrates a perspective view of the adjustable rod assembly of FIG. 4.

A third preferred embodiment of adjustable rod assembly 10 is shown in FIGS. 4 and 5 and has two of the clamping assemblies 51 described in connection with FIG. 1. One clamping assembly 51 is attached to one end of the adjusting assembly 15 while a second clamping assembly 51 is attached to the other end of the adjusting assembly 15. The elongate members 20, 30 making up the adjusting assembly 15 in the embodiment of FIG. 1 are shown as being substantially straight, while the elongate members 20, 30 making up the adjusting assembly 15 in the embodiment of FIGS. 2-5 are slightly curved, having a kyphotic curvature when attached to the ribs, pelvis or vertebrae. In this regard, the ends of the curved elongate members are bent inward toward the inner surface of the elongate member 20, 30. When the adjustable rod assembly is attached to the posterior side of the back of the rib cage and/or posterior side of vertebrae (lamina) or posterior side of the pelvis (as shown in FIG. 3) the radius of curvature is toward and defined by the inner surface of the elongate members forming a kyphotic curvature. The locking element or coupler 40 which snaps over the outer surface of the adjustable assembly 15 faces the posterior side of the patient as shown in FIG. 3.

Figure 15:
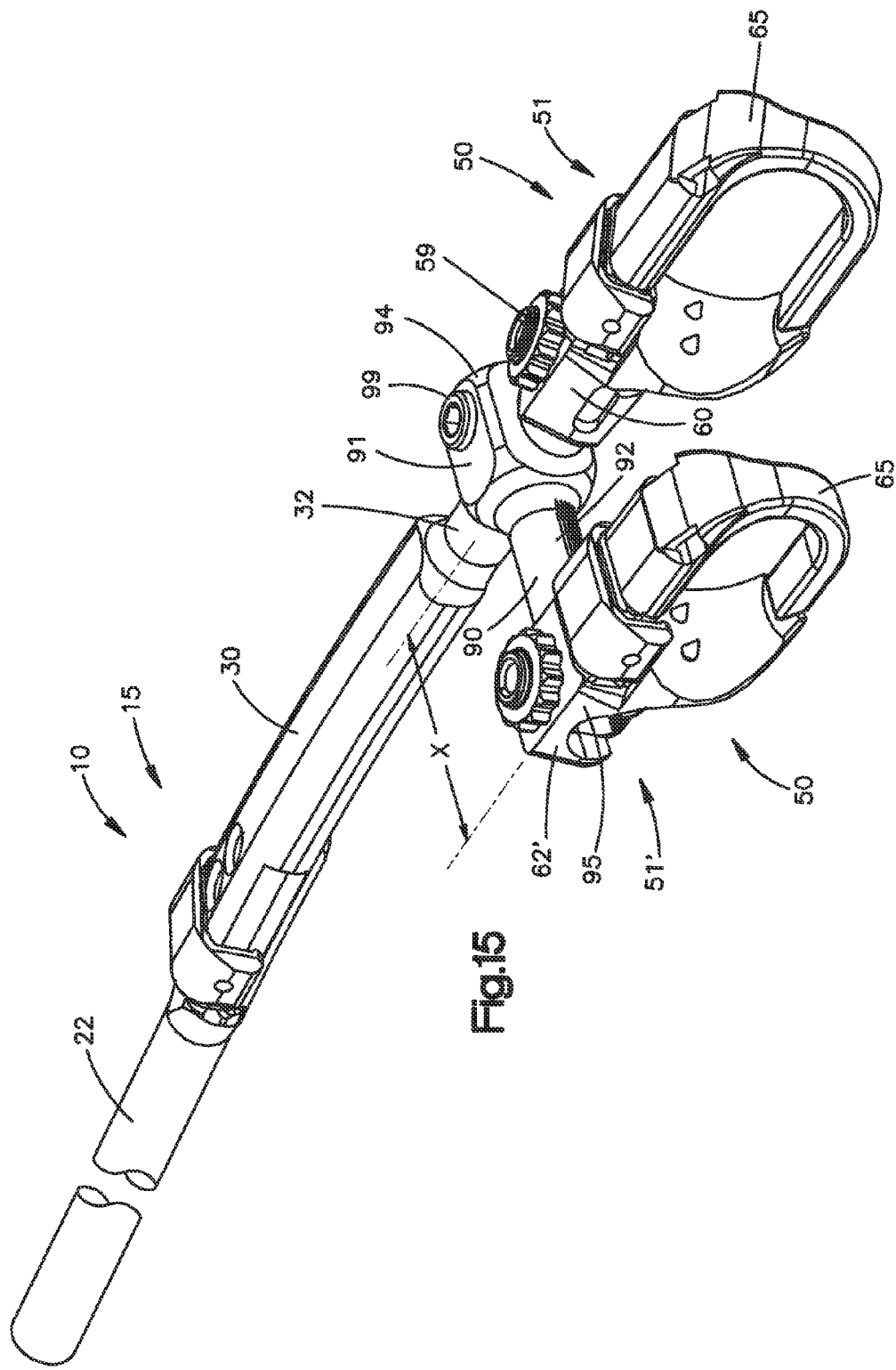
FIG. 15 illustrates a perspective view of a portion of an adjustable rod assembly in accordance with a fourth preferred embodiment of the present invention.
Figure 16:
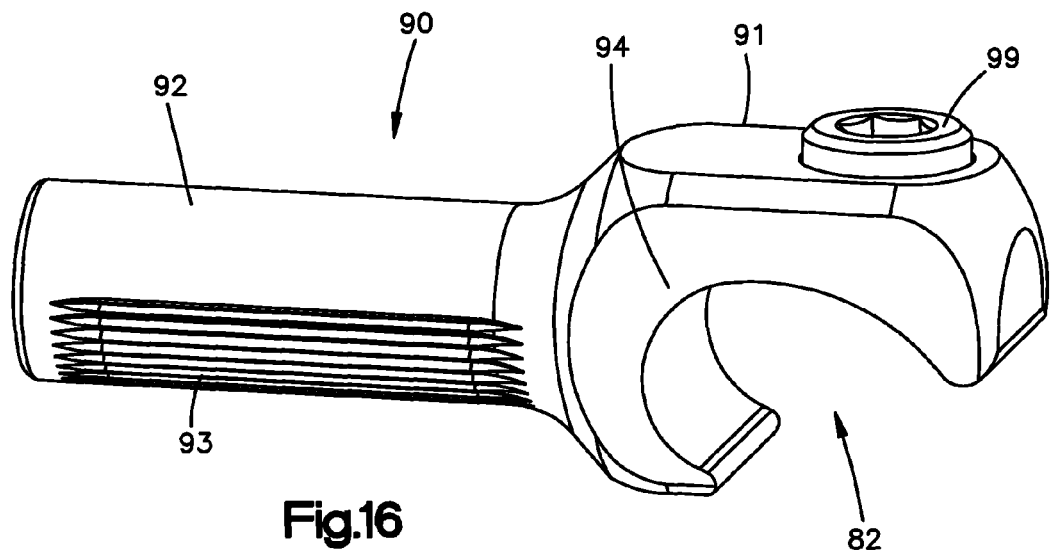
FIG. 16 illustrates a side perspective view of the transverse connector of the adjustable rod assembly of FIG. 14.

A fourth preferred embodiment of adjustable rod assembly 10 is shown in FIG. 15. The adjustable rod assembly in FIG. 15 includes adjusting assembly 15, a bone connecting element (not shown) connected to rod portion 22, a bone connecting element 50 attached to rod portion 32, and a second bone connecting element 50 operatively associated with the rod portion 32. The bone connecting element 50 attached directly to the end of the rod portion 32 is the clamping assembly 51 described in connection with the adjustable rod assembly of FIG. 1. As illustrated in FIGS. 1-5, 12-12B and 15, the angular orientation of the clamping assembly 51 can be adjusted by rotating the clamping assembly 51 about the longitudinal axis L of the rod portion 32 and turning the nut 17 to move the locking element 59 to fix the position of the clamping assembly 51 relative to the elongate member 30.

Figure 17:
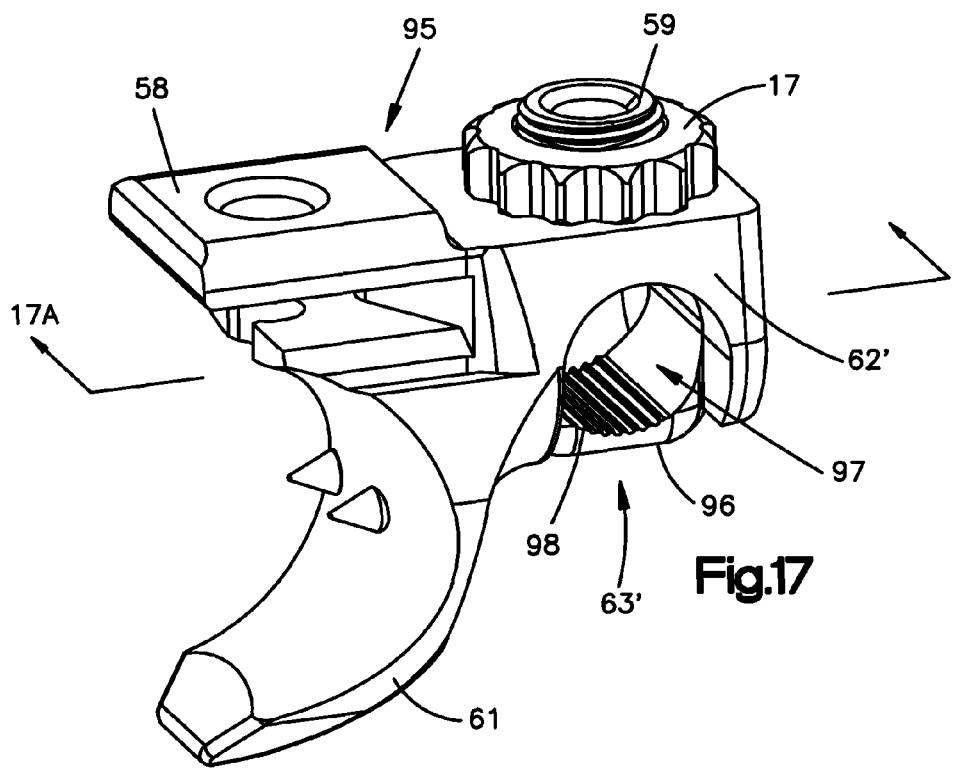
FIG. 17 illustrates a perspective side view of the transverse rib hook of the adjustable rod assembly of FIG. 15.

The bone connecting element 50 operatively associated with the rod portion 32 of the elongate member 30 is clamping assembly 51' which is similar to clamping assembly 51. The clamping assembly 51' includes a rib hook 95 and rib hook cap 65. The rib hook cap 65 in clamping assembly 51' is the same as the rib hook cap 65 in clamping assembly 51. The transverse rib hook 95 as shown in FIGS. 17-17B is substantially similar to rib hook 60 and includes the same hook portion 61 but a slightly modified connecting portion 62'. Instead of having a recess 63 at the distal end of the body 62 which is aligned with the longitudinal axis 12A-12A of the rib hook 60 as in clamping assembly 51, connecting portion 62' of transverse rib hook 95 includes an open channel 63' in the connecting portion 62' that is open at the bottom and sides of body 62' to form a U-shaped channel. Channel 63' is not open at the distal end or back of body 62' as with opening 63 in rib hook 60. Leg portion 96 of the locking element 59 closes channel 63' and is movable in order to adjust the size of the opening 97 provided by the open channel 63' and the leg portion 96. Operation of nut 17 moves locking element 59 which moves the leg portion 96 of the locking element 59 to adjust the size of the opening 97. The body 62' and the leg portion 96 form a clamp to fix and lock the transverse rib hook 95 to transverse bar 90. The opening 97 formed by the locking element 59 and body 62' in rib hook 95 is generally transverse to and preferably perpendicular to the opening 16 formed by the locking element 59 and body 62 in rib hook 60. Alternatively, instead of nut 17 and locking element 59, a set screw as described above in connection with rib hook 60 of FIGS. 12-12B may be used to abut against and fix the position of the transverse rib hook 95 with respect to transverse bar 90.

The clamping assembly 51' is laterally offset and preferably generally parallel to the clamping assembly 51. Transverse bar 90 is provided to laterally offset the clamping assembly 51'. The transverse bar 90 includes a clamping portion 91 and a shaft portion 92. The shaft portion 92 is preferably round and cylindrically shaped. The shaft portion 92 is receivable within the opening 97 formed in the transverse rib hook 95 by the channel 63' and the leg portion 96. The shaft portion 92 is slideable within the opening 97 of the transverse rib hook 95 to adjust the amount of lateral offset, i.e., the distance X that the bone connecting clamping assembly 51' is spaced from the clamping assembly 51. The transverse rib hook 95 is also angularly adjustable with respect to the transverse hook 90 by rotating the transverse rib hook 95 about the shaft portion 92. The position of the transverse rib hook 95 along the length of the transverse hook 90 and the angular orientation of the transverse rib hook 95 with respect to the transverse hook 90 may be adjusted and thereafter fixed by turning the nut 17 to move the locking element 59 in the transverse rib hook 95 to clamp the shaft portion 92 between the leg portion 96 and the connecting portion 62'. Serrations 93 may be provided in the shaft portion 92 to interact with serrations 98 formed on leg portion 96. The serrations 93, 98 may assist in the clamping action of the shaft portion 92 in the transverse rib hook 95 and/or provide detents to provide predetermined angular orientations. For example, the serrations 93, 98 can be provided at predetermined angular intervals, such as, for example, 5° intervals, so that the surgeon can vary the angular position of the transverse rib hook 95 in known intervals.

The clamping portion 91 of the transverse bar 90 may include a hook portion 94 that includes an opening 82 sized and configured to receive the rod portion 22, 32 of the elongate members 20, 30. In FIG. 15, the opening 82 of the transverse bar 90 is fitted over and clamped to rod portion 32 of elongate member 30 but it can be appreciated that one or more additional transverse bars 90 and clamping assemblies 51' can be attached to rod portions 22 or 32. A set screw 99 is tightened to fix the position of the transverse hook 90 on the rod portion. The transverse hook 90 can angularly adjust with respect to the rod portion and can slide along the length of the rod portion to adjust the position and orientation of clamp assembly 51' with respect to the adjusting assembly 15 and the elongate members 20, 30. The transverse bar 90 is substantially similar to the transverse bar described and illustrated in U.S. Pat. No. 7,118,571, the contents of which are incorporated by reference in their entirety herein.

While the adjustable rod assembly 10 in FIG. 15 is shown as having two bone connecting elements 50 attached to elongate member 30 it can be appreciated that transverse bar 90 and bone connecting assembly 51' can be utilized without bone connecting clamping assembly 51. Alternatively, additional transverse bars 90 and bone clamping assemblies 51' can be utilized with the embodiment of FIG. 15, or the embodiments of FIGS. 1-6, either attached to rod portion 32 or attached at the other end of the adjustable rod assembly 10 to rod portion 22. The transverse bar 90 and clamp assembly 51' permit the adjustable rod assembly to attach at separate locations along the same rib, and/or permit the same end of the elongate member, e.g., rod portion 32, to attach to multiple ribs.

Any one of bone connecting elements 50 may be attached to elongate members 20, 30 including, but not limited to, lamina hook 70, S-hooks 75, clamping assemblies 51 and 51'. Other bone connecting elements not shown may also be utilized in the adjustable rod assembly, such as, for example, pedicle screws or pedicle hooks. The pedicle screws preferably would have a screw portion for engaging the bone and a body with a rod-receiving channel and a locking mechanism to lock the elongate member 20, 30 in position in the rod-receiving channel. The pedicle hooks preferably would have a hook portion for engaging and attaching to bone and a body with a rod-receiving channel and a locking mechanism to lock the elongate member 20, 30 in position in the rod-receiving channel. Exemplary embodiments of pedicle screws include those described in International Patent Application No. PCT/US2008/070670, filed on Jul. 21, 2008, entitled "Polyaxial Bone Fixation Element", International Patent Application No. PCT/US2006/015692, filed on Apr. 25, 2006, entitled "Bone Anchor with Locking Cap and Method of Spinal Fixation", and International Patent Application No. PCT/CH1997/00236, filed on Jun. 16, 1997, entitled "Device for Connecting a Longitudinal Support with a Pedicle Screw", the contents of which are hereby incorporated by reference in their entirety. It should be understood however that the present invention is not limited in use to any particular type of pedicle screw.

The bone connecting elements 50 can be formed of a number of biocompatible materials, such as, for example, titanium, stainless steel, titanium alloy, cobalt-chrome, composites, ceramics, PEEK, or other polymers. These materials are not limiting and the bone-connecting elements may be constructed of nearly any biocompatible material that is able to take on the desired shape and withstand the normal operating conditions (e.g., environmental and physical property requirements) of the bone connecting elements 50.

In operation, the adjustable rod 10 can be used alone or in conjunction with a rib cage corrective device or conventional screw/hook system known in the art. To mount the adjustable rod assembly 10 to a patient's spine, rib cage and/or pelvis in the preferred embodiment, two bone connecting elements 50 are implanted. The extension adjusting assembly 15 can be assembled preoperatively by coupling the first elongate member 20 to the second elongate member 30 by sliding the male expansion portion 24 into the female expansion portion 34 and aligning at least one of the plurality of through holes 31 with at least one of the plurality of blind boreholes 21 and placing the locking element 40 over the female expansion portion 34 and through a pair of aligned through holes 31 and blind holes 21. The length of the adjustable rod assembly 10 is adjustable via the choice of aligned holes 31/21. The first rod portion 22 and the second rod portion 32 are then coupled to the rod-receiving portions of the previously implanted bone connecting elements 50. The angular orientation of the bone connecting elements 50 relative to the rod portions 22, 32 may be adjusted pre-operatively or during the procedure. Post operative adjustments to the expandable rod assembly 10 to accommodate growth of a developing spine or progressive correction of a deformed spine can be performed by making a small opening near the locking element 40, uncoupling the locking element 40 from the extension adjusting assembly 15, distracting the first elongate member 20 from the second elongate member 30, and recoupling the locking element 40 to an alternate pair of aligned holes 31/21.

In an alternate method of mounting the preferred adjustable rod assembly 10 to a patient's spine, ribcage and/or pelvis, the adjustable rod assembly 10 can be implanted in a minimally invasive manner and assembled in situ. In this preferred method, two bone connecting elements 50 are implanted via small openings, preferably formed by small incisions. The first and second elongate members 20, 30 are then inserted through one or more small openings, which in one embodiment can be the same small incisions used to implant the pair of bone connecting elements. The first and second elongate members 20, 30 then may be coupled to the bone connecting elements. The first and second elongate members 20 and 30 are then coupled using the locking element 40 via a third small opening, preferably a third small incision. In addition, this method may be performed through a mini-opening formed in the patient.

The first and second rod portions 22, 32, as well as the male and female expansion sections 24, 34, can be provided in a range of different curvatures to match the desired lordotic/kyphotic attributes for the adjustable rod assembly 10. The elongate members 20, 30 also can be straight. Combinations of curved and straight portions are also contemplated. For example, the rod portions 22, 32 can be straight while the extension portions are curved, or vice versa, the extension portions can be straight and the rod portions curved. Alternatively the entire elongate members may be curved, or the entire elongate members may be straight. Preferably, if the extension portions 24, 34 are curved, they both have substantially the same curvature, preferably in the regions where they overlap or telescope one elongate member with respect to the other elongate member.

The adjusting assemblies 15 may be supplied as a kit with multiple pieces in different sizes and curvatures. For example, multiple elongate members 20, and multiple elongate members 30 can be provided each with a different radii of curvature, such as for example, a set with 220 mm radius and a set with 500 mm radius. In addition each elongate member with a different radius of curvature may be provided in multiple different lengths, and multiple different thickness so that different size patients can be treated. The first and second rod portions 22, 32, as well as the male and female expansion sections 24, 34, can also be provided in a range of different lengths. The first and second rod portions 22, 32, as well as the male and female expansion sections 24, 34, can also be provided in a range of different rigidities, or may include damping elements to provide dynamic stabilization to desired spinal levels. The first and second rod portions 22, 32 also may be formed with differing diameters, e.g., 4.5 mm and 6.0 mm, such that a low profile bone connecting element 50 can couple to the first rod portion 22 and a more robust bone connecting element can couple to the second rod portion 32, or vice versa.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention is not limited to the particular embodiments shown but may be embodied in other specific forms, structures, arrangements, proportions, and with other elements, materials, and components, without departing from the spirit or essential characteristics thereof. One skilled in the art will appreciate that the invention may be used with many modifications of structures, arrangement, proportions, materials, and components used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

We claim:

1. An adjustable rod assembly configured to straighten a spine, the adjustable rod assembly comprising:
   a bone connecting element configured to attach to a rib, the bone connecting element including a first portion and a second portion, the first portion configured to fit at least partially around the rib, the second portion including a first opening and a second opening that intersects the first opening, wherein the first opening extends along a direction into the bone connecting element and terminates within the bone connecting element at a base surface of the bone connecting element;
   a rod portion that is elongate along an axis, the rod portion configured to be inserted into the first opening such that the bone connecting element is rotatable with respect to the rod portion about the axis; and
   a locking element configured to be inserted into the second opening such that in a first configuration the bone connecting element is rotatable with respect to the rod portion about the axis, and in a second configuration the bone connecting element is secured to the rod portion such that rotation of the bone connecting element with respect to the rod portion about the axis is prevented.

2. The adjustable rod assembly of claim 1, wherein the locking element defines a third opening configured to receive the rod portion, and in the first configuration the third opening is aligned with the first opening.

3. The adjustable rod assembly of claim 2, wherein the direction is a first direction, the first opening extends into the second portion along the first direction and the second opening extends into the second portion along a second direction that is perpendicular to the first direction.

4. The adjustable rod assembly of claim 3, wherein the locking element is translatable relative to the bone connecting element.

5. The adjustable rod assembly of claim 4, wherein the locking element includes a nut that is configured to be actuated thereby causing the third opening to translate with respect to the bone connecting element along the second direction thereby causing the adjustable rod assembly to transition between the first configuration and the second configuration.

6. The adjustable rod assembly of claim 5, wherein the bone connecting element includes a first member that includes the first portion and the second portion, and the bone connecting element includes a second member configured to be connected to the first member such that the first portion of the first member and the second member cooperate to define a fourth opening that is configured to fit at least partially around the rib.

7. The adjustable rod assembly of claim 5, wherein the bone connecting element is a first bone connecting element, the rib is a first rib, and the rod portion is a first rod portion, the adjustable rod assembly further comprising:
   a first elongate member that includes the first rod portion, the first elongate member further includes a first expansion portion;
   a second bone connecting element configured to be attached to a second rib, a pelvis, or a spine; and
   a second elongate member including a second rod portion configured to be coupled to the second bone connecting element, the second elongate member including a second expansion portion slidably moveable with respect to the first expansion portion.

8. The adjustable rod assembly of claim 7, wherein the first expansion portion includes a plurality of bore holes in an outer surface of the first expansion portion, the second expansion portion includes a plurality of through holes in an outer surface of the second expansion portion, and the adjustable rod assembly further comprises:
   a locking element configured to be inserted into at least one of each of the plurality of bore holes and the plurality of through holes to thereby couple the first elongate member and the second elongate member together thereby fixing a length of the adjustable rod assembly measured from the first bone connecting element to the second bone connecting element.

9. An adjustable rod assembly configured to straighten a spine, the adjustable rod assembly comprising:
   a bone connecting element configured to attach to a rib, the bone connecting element including a member configured to fit at least partially around the rib, the member including an inner surface that at least partially defines a first opening, wherein the first opening extends towards the member along a direction and terminates within the bone connecting element at a base surface of the bone connecting element;
   a rod portion, the rod portion configured to be inserted into the first opening; and
   a locking element coupled to the bone engaging element such that the locking element is translatable with respect to the bone engaging element, the locking element defining a second opening configured to receive the rod portion such that the rod portion is rotatable with respect to both the locking element and the bone connecting element;
   wherein when the rod portion is inserted into the second opening, translation of the locking element with respect to the bone engaging element causes the rod portion to abut the inner surface thereby coupling the rod portion to the bone connecting element such that rotation of the rod portion with respect to both the locking element and the bone connecting element is prevented.

10. The adjustable rod assembly of claim 9, wherein the member defines a third opening, and the locking element is configured to be inserted into the third opening.

11. The adjustable rod assembly of claim 10, wherein the direction is a first direction, the first opening extends into the member along the first direction and the third opening extends into the second portion along a second direction that is perpendicular to the first direction.

12. The adjustable rod assembly of claim 11, wherein the locking element includes a nut that is configured to be actuated thereby causing the second opening to translate with respect to the member along the second direction thereby causing the rod portion to abut the inner surface thereby coupling the rod portion to the bone connecting element such that rotation of the rod portion with respect to both the locking element and the bone connecting element is prevented.

13. The adjustable rod assembly of claim 12, wherein the member is a first member, the bone connecting element includes a second member configured to be connected to the first member such that the first member and the second member cooperate to define a fourth opening that is configured to fit at least partially around the rib.

14. The adjustable rod assembly of claim 12, wherein the bone connecting element is a first bone connecting element, the rib is a first rib, the rod portion is a first rod portion, and the adjustable rod assembly further comprises:
    a first elongate member that includes the rod portion and a first expansion portion;
    a second bone connecting element configured to be attached to a second rib, a pelvis, or a spine; and
    a second elongate member including a second rod portion configured to be coupled to the second bone connecting element, the second elongate member including a second expansion portion slidably moveable with respect to the first expansion portion.

15. The adjustable rod assembly of claim 14, wherein the first expansion portion includes a plurality of bore holes in an outer surface of the first expansion portion, the second expansion portion includes a plurality of through holes in an outer surface of the second expansion portion, and the adjustable rod assembly further comprises:
    a locking element configured to be inserted into at least one of each of the plurality of bore holes and the plurality of through holes to thereby couple the first elongate member and the second elongate member together thereby fixing a length of the adjustable rod assembly measured from the first bone connecting element to the second bone connecting element.

16. A method of implanting an adjustable rod assembly, the method comprising the steps of:
    coupling a bone connecting element of the adjustable rod assembly to a first bone, wherein the first bone is a rib, the coupling step including the steps of:
        seating a first member of the bone connecting element adjacent the rib such that the first member defines a portion of a first opening that fits at least partially around the rib; and
        after the step of seating the first member, seating a second member of the bone connecting element adjacent the rib such that the first member and the second member cooperate to define the first opening that fits at least partially surround the rib;
    inserting a rod portion of an elongate member of the adjustable rod assembly along a direction into a second opening that 1) is defined by an inner surface of the bone connecting element, and 2) terminates within the bone connecting element at a base surface of the bone connecting element, thereby coupling the elongate member to the bone connecting element;
    rotating the bone connecting element relative to the elongate member about a longitudinal axis of the bone connecting element; and
    fixing the bone connecting element with respect to the elongate member about the longitudinal axis.

17. The method of claim 16, further comprising the steps of:
    coupling a locking mechanism of the adjustable rod assembly to the bone connecting element; and
    coupling the elongate member to the locking mechanism.

18. The method of claim 17, wherein the fixing step includes the step of translating the locking mechanism with respect to the bone connecting element.

19. The method of claim 18, wherein the translating step includes the step of translating the elongate member with respect to the bone connecting element thereby causing the elongate member to abut the bone connecting element and fix the bone connecting element with respect to the elongate member about the longitudinal axis.

20. The method of claim 16, wherein the bone connecting element is a first bone connecting element, the elongate member is a first elongate member, the longitudinal axis is a first longitudinal axis, the method further comprising the steps of:
    coupling a second bone connecting element of the adjustable rod assembly to a second bone, wherein the second bone is different than the first bone;
    coupling a second elongate member of the adjustable rod assembly to the second bone connecting element;
    rotating the second bone connecting element relative to the second elongate member about a second longitudinal axis of the second bone connecting element; and
    fixing the second bone connecting element with respect to the second elongate member about the second longitudinal axis.

* * * * *